United States Patent [19]

Hornback et al.

[11] Patent Number: 5,624,934

[45] Date of Patent: Apr. 29, 1997

[54] PROTEASE INHIBITORS

[75] Inventors: William J. Hornback; John E. Munroe; Timothy A. Shepherd, all of Indianapolis, Ind.

[73] Assignee: Eli Lilly and Company, Indianapolis, Ind.

[21] Appl. No.: 515,875

[22] Filed: Aug. 16, 1995

Related U.S. Application Data

[60] Division of Ser. No. 299,186, Aug. 31, 1994, Pat. No. 5,480,887, which is a continuation-in-part of Ser. No. 190,810, Feb. 2, 1994, abandoned.

[51] Int. Cl.⁶ ..................... A61K 31/435; C07D 495/04
[52] U.S. Cl. .................. 514/301; 514/300; 514/302; 546/113; 546/114; 546/115; 546/122
[58] Field of Search ..................... 546/113, 114, 546/115, 122; 514/300, 301, 302

[56] References Cited

U.S. PATENT DOCUMENTS

| | | | |
|---|---|---|---|
| 5,142,056 | 8/1992 | Kempe et al. | 546/265 |
| 5,484,926 | 1/1996 | Dressman et al. | 546/114 |

FOREIGN PATENT DOCUMENTS

| | | |
|---|---|---|
| 0337714 | 10/1989 | European Pat. Off. . |
| 0346847 | 12/1989 | European Pat. Off. . |
| 0361341 | 4/1990 | European Pat. Off. . |
| 0498680 | 8/1992 | European Pat. Off. . |
| 0526009 | 2/1993 | European Pat. Off. . |
| 0539192 | 4/1993 | European Pat. Off. . |
| WO92/08701 | 5/1992 | WIPO . |
| WO93/13066 | 7/1993 | WIPO . |

OTHER PUBLICATIONS

Roberts N.A. et al., Science, 248, 358–361 (20 Apr. 1990).
Thaisrivongs S. et al., J. Med. Chem., 34, 2344–2356 (1991).
Ghosh A.K. et al., J. Med. Chem., 37, 1177–1188 (1994).
Ghosh A.K. et al., J. Med. Chem., 37, 2506–2508 (1994).
Kim B.M., et al., Tetrahedron Letters, 34(41), 6517–6520 (1993).

*Primary Examiner*—Bernard Dentz
*Attorney, Agent, or Firm*—Birch, Stewart, Kolasch & Birch, LLP

[57] ABSTRACT

The present invention provides novel HIV protease inhibitors, pharmaceutical formulations containing those compounds and methods of treating and/or preventing HIV infection.

36 Claims, No Drawings

PROTEASE INHIBITORS

CROSS-REFERENCE TO RELATED APPLICATIONS

This application is a division of U.S. patent application Ser. No. 08/299,186, filed Aug. 31, 1994 now U.S. Pat. No. 5,480,887, which is a continuation-in-part of U.S. patent application Ser. No. 08/190,810, filed Feb. 2, 1994, now abandoned.

BACKGROUND OF THE INVENTION

A retrovirus designated human immuno-deficiency virus (HIV) is the causative agent of the complex disease termed Acquired Immune Deficiency Syndrome (AIDS), and is a member of the lentivirus family of retroviruses. M. A. Gonda, F. Wong-Staal, R. C. Gallo, "Sequence Homology and Morphological Similarity of HTLV III And Visna Virus, A Pathogenic Lentivirus", Science, 227, 173, (1985); P. Sonigo, N. Alizon, et al., "Nucleotide Sequence of the Visna Lentivirus: Relationship to the AIDS Virus", Cell, 42, 369, (1985). The complex disease AIDS includes progressive destruction of the immune system and degeneration of the central and peripheral nervous systems. The HIV virus was previously known or referred to as LAV, HTLV-III or ARV.

A common feature of retrovirus replication is the post-translational processing of precursor polyproteins by a virally encoded protease to generate mature viral proteins required for viral assembly and function. Interruption of this processing appears to prevent the production of normally infectious virus. Unprocessed structural proteins also have been observed in clones of non-infectious HIV strains isolated from human patients. The results suggest that the inhibition of HIV protease represents a viable method for the treatment or prevention of AIDS and/or treatment or prevention of infection by HIV.

The HIV genome encodes structural protein precursors known as gag and pol, which are processed to afford the protease, reverse transcriptase and endonuclease/integrase. The protease further cleaves gag and gag-pol polyproteins to yield mature structural proteins of the virus core.

Considerable efforts are being directed toward the control of HIV by means of the structural protein precursors which are processed to yield the retroviral protease, reverse transcriptase and endonuclease/integrase. For example, a currently used therapeutic, AZT, is an inhibitor of the viral reverse transcriptase. H. Mitsuya, NS. Broder, "Inhibition of the In Vitro Infectivity in Cytopathic Effects of HTLV III", Proc. Natl. Acad. Sci. USA, 83, 1911 (1986).

Research efforts have also been directed toward HIV protease inhibitors. For example, European Patent Application (EPA) 361 341; EPA 346 847; EPA 402 646; and EPA 337 714 all disclose compounds which are said to be useful as HIV protease inhibitors.

Unfortunately, many of the known HIV protease inhibitors suffer from toxicity problems, lack of bioavailability or short in vivo half-lives. In particular, it is believed that oral bioavailability is a necessary characteristic of an HIV protease inhibitor due to the chronic nature of the disease. However, peptides and peptide mimetics are notorious for their inability to be orally absorbed. Thus, despite the recognized therapeutic potential associated with a protease inhibitor and the research efforts expended thus far, a viable therapeutic agent has not yet emerged.

Accordingly, a primary object of the present invention is to provide novel HIV protease inhibitors that possess desirable biological properties relative to previous HIV protease inhibitors while retaining potent HIV protease inhibitory activity. Thus, these HIV protease inhibitors promise to be useful for inhibiting HIV replication in an HIV infected cell, a cell susceptible to HIV infection or a primate in need thereof, thus treating and/or preventing HIV infection.

A further object of the present invention is to provide therapeutic compositions that are of value in the treatment and/or prevention of HIV infection.

Still another object is to provide methods for the treatment and/or prevention of HIV infection.

Other objects, features and advantages will become apparent to those skilled in the art from the following description and claims.

SUMMARY OF THE INVENTION

The present invention relates to compounds of formula (I), below, and pharmaceutically acceptable salts thereof that inhibit the protease encoded by human immunodeficiency virus (HIV) type 1 (HIV-1) or type 2 (HIV2). These compounds are useful in the treatment and/or prevention of infection by HIV. The compounds, their pharmaceutically acceptable salts, and the pharmaceutical compositions of the present invention can be used alone or in combination with other antivirals, immunomodulators, antibiotics or vaccines. Methods of treating or preventing AIDS, methods of treating or preventing HIV infection and methods of inhibiting HIV replication are disclosed.

The present invention relates to a method for inhibiting HIV replication in an HIV infected cell, a cell susceptible to HIV infection or a primate in need thereof, thus treating and/or preventing HIV infection, comprising administering an effective amount of a compound of formula (I):

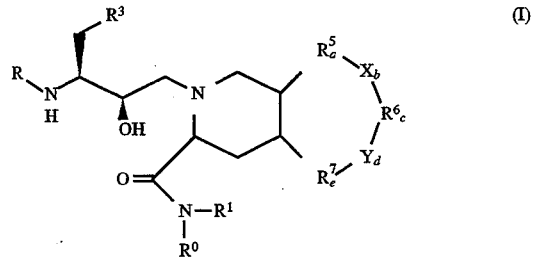

wherein:
R is a group having the formula:

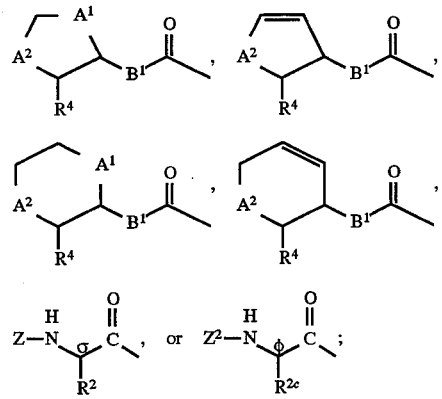

Z is hydrogen, carbamoyl, formyl, $C_2$–$C_6$ alkanoyl, $C_1$–$C_4$ alkoxycarbonyl, —C(O)CF$_3$ or —S(O)$_2$—Z$^1$;
Z$^1$ is $C_1$–$C_6$ alkyl, amino, $C_1$–$C_4$ alkylamino, trifluoromethyl or di($C_1$–$C_4$)alkylamino;

$Z^2$ is quinolinyl-C(O)—, naphthyloxymethyl-C(O)—, substituted quinolinyl-C(O)—, or substituted naphthyloxymethyl-C(O)—;

σ, an asymmetric center, is in a non-naturally occurring configuration;

φ, an asymmetric center, is in a naturally occurring configuration;

$R^2$ is an amino acid side chain or —$(CH_2)_y$—$W^1$—$R^{2a}$;

y is 0, 1 or 2;

$W^1$ is a bond, divalent $(C_2-C_4)$alkenyl, divalent $(C_2-C_4)$alkynyl, —C(O)—O—, —O—C(O)—, —C(O)—$NR^{2b}$—, —$NR^{2b}$—C(O)—, —$NR^{2b}$—, —C(O)—, —O—, —S—, —S(O)— or —$S(O)_2$—;

$R^{2a}$ is aryl, unsaturated heterocycle, heterocycle, aryl $(C_1-C_4)$alkyl, unsaturated heterocycle$(C_1-C_4)$alkyl, heterocycle$(C_1-C_4)$alkyl, tetrazolyl, N-$(C_1-C_4)$ alkyltetrazolyl or N-(aryl)tetrazolyl;

$R^{2b}$ is hydrogen or $C_1-C_4$ alkyl;

$R^{2c}$ is an amino acid side chain;

$A^1$ and $A^2$ are independently —C—, —O—, —S—, —S(O)—, —$S(O)_2$—, —NH— or —N(CH_3)—;

$B^1$ is —O—, —S—, —$CH_2$—, —$CH_2$—$CH_2$—, —NH—, or —N(CH_3)—;

$R^4$ is $C_1-C_6$ alkyl;

$R^3$ is —$(CH_2)_i$—$R_{3a}$;

i is 0, 1, 2, 3, or 4;

$R^{3a}$ is aryl, —O-aryl, or —S-aryl;

$R^0$ and $R^1$ are independently hydrogen, $C_1-C_6$ alkyl, or hydroxy$(C_1-C_6)$alkyl;

a, c and e are each independently 0, 1 or 2;

b and d are each independently 0 or 1;

each $R^5$ is independently —$CH_2$—, —$CHR^{5x}$—, or —$CR^{5x}R^{5x}$—;

each $R^6$ is independently —$CH_2$—, —$CHR^{6x}$—, or —$CR^{6x}R^{6x}$—;

each $R^7$ is independently —$CH_2$—, —$CHR^{7x}$—, or —$CR^{7x}R^{7x}$—;

each of $R^{5x}$, $R^{6x}$, and $R^{7x}$ is independently selected from the group consisting of halo, hydroxy, $C_1-C_6$ alkyl, halo$(C_1-C_6)$alkyl, hydroxy$(C_1-C_6)$alkyl, $C_1-C_6$ alkoxy, $C_1-C_6$ alkylthio, $C_1-C_6$ alkylthio $(C_1-C_6)$alkyl, amino, or cyano;

X and Y are independently —S—, —S(O)—, —$S(O)_2$—, —O—, —NH—, or —$N(R^9)$—; and $R^9$ is $C_1-C_6$ alkyl, aryl$(C_1-C_6)$alkyl, aryl, arylcarbonyl, formyl, or $C_2-C_6$ alkanoyl;

with the provisos that:

b and d cannot both be 0;

the sum of a, b, c, d and e must be 2, 3, 4 or 5;

if $R^5$ is —$CR^{5x}R^{5x}$—, then $R^6$ must be —$CH_2$— or —$CHR^{6x}$—; and $R^7$ must be —$CH_2$— or —$CHR^{7x}$—;

if $R^6$ is —$CR^{6x}R^{6x}$—, then $R^5$ must be —$CH_2$— or —$CHR^{5x}$—; and $R^7$ must be —$CH_2$— or —$CHR^{7x}$—;

if $R^7$ is —$CR^{7x}R^{7x}$—, then $R^5$ must be —$CH_2$— or —$CHR^{5x}$—; and $R^6$ must be —$CH_2$— or —$CHR^{6x}$—;

or a pharmaceutically acceptable salt thereof.

The present invention also relates to a compound of formula (I), or a pharmaceuytically acceptable salt thereof wherein $R_0$, R, $R^1$, $R^3$, $R^5$, $R^6$, $R^7$, a, b, c, d, and e are as defined above in formula (I).

The present invention further provides pharmaceutical formulations comprising a compound of formula (I) or a pharmaceutically acceptable salt thereof, in combination with a pharmaceutically acceptable carrier, diluent or excipient therefor.

DETAILED DESCRIPTION OF THE INVENTION

The present invention provides new compounds of formula (I), as described above, that are useful for treating and/or preventing HIV infection and/or AIDS.

All temperatures stated herein are in degrees Celsius (°C.). All units of measurement employed herein are in weight units except for liquids which are in volume units.

The term "$C_1-C_6$ alkyl" represents a straight or branched alkyl chain having from one to six carbon atoms. Typical $C_1-C_6$ alkyl groups include methyl, ethyl, propyl, isopropyl, butyl, isobutyl, sec-butyl, t-butyl, pentyl, neo-pentyl, hexyl, and the like. The term "$C_1-C_6$ alkyl" includes within its definition the term "$C_1-C_4$ alkyl".

"Divalent$(C_2-C_4)$alkenyl" represents a straight or branched divalent alkenyl chain having from two to four carbon atoms. Typical divalent$(C_2-C_4)$alkenyl groups include ethenyl, 1-propenyl, 2-propenyl, 1-butenyl, 2-butenyl and the like.

"Divalent$(C_2-C_4)$alkynyl" represents a straight or branched divalent alkynyl chain having from two to four carbon atoms. Typical divalent$(C_2-C_4)$alkynyl groups include ethynyl, 1-propynyl, 2-propynyl, 1-butynyl, 2-butynyl and the like.

The term "halo" represents chloro, fluoro, bromo or iodo.

The term "halo$(C_1-C_6)$alkyl" represents a straight or branched alkyl chain having from one to six carbon atoms with 1-3 halogen atoms attached to it. Typical halo$(C_1-C_6)$ alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl, 6-bromohexyl, and the like.

The term "hydroxy$(C_1-C_6)$alkyl" represents a straight or branched alkyl chain having from one to six carbon atoms with a hydroxy group attached to it. Typical hydroxy$(C_1-C_6)$ alkyl groups include hydroxymethyl, 2-hydroxyethyl, 3-hydroxypropyl, 2-hydroxyisopropyl, 4-hydroxybutyl, 2-hydroxyhexyl, and the like.

The term "$C_1-C_6$ alkylthio" represents a straight or branched alkyl chain having from one to six carbon atoms attached to a sulfur atom. Typical $C_1-C_6$ alkylthio groups include methylthio, ethylthio, propylthio, isopropylthio, butylthio, sec-butylthio, t-butylthio, pentylthio, hexylthio, and the like.

The term "$C_1-C_6$ alkylthio$(C_1-C_6)$alkyl" represents a straight or branched $C_1-C_6$ alkyl chain having from one to six carbon atoms with a $C_1-C_6$ alkylthio moiety attached to it. Typical $C_1-C_6$ alkylthio$(C_1-C_6)$alkyl groups include methylthiomethyl, ethylthiomethyl, propylthioethyl, isopropylthiomethyl, butylthiopentyl, sec-butylthiomethyl, hexylthiopropyl, and the like.

The term "$C_1-C_4$ alkylamino" represents a straight or branched alkyl chain having from one to four carbon atoms attached to an amino group. Typical $C_1-C_4$ alkylamino groups include methylamino, ethylamino, propylamino, isopropylamino, butylamino, sec-butylamino, and the like.

The term "di$(C_1-C_4)$alkylamino" represents two straight or branched alkyl chains, each having from one to four carbon atoms attached to a common amino group. Typical di$(C_1-C_4)$alkylamino groups include dimethylamino, ethylmethylamino, methylpropylamino, ethylisopropylamino, butylmethylamino, sec-butylethylamino, and the like.

The term "$C_1-C_6$ alkoxy" represents a straight or branched alkyl chain having from one to six carbon atoms attached to an oxygen atom. Typical $C_1$–$C_6$ alkoxy groups include methoxy, ethoxy, propoxy, isopropoxy, butoxy, sec-butoxy, t-butoxy, pentoxy, hexoxy, and the like.

The term "$C_1$–$C_4$ alkoxycarbonyl" represents a straight or branched alkoxy chain having from one to four atoms attached to a carbonyl moiety. Typical $C_1$–$C_4$ alkoxycarbonyl groups include methoxycarbonyl, ethoxycarbonyl, propoxycarbonyl, isopropoxycarbonyl, butoxycarbonyl, and the like.

"$C_2$–$C_6$ alkanoyl" represents a straight or branched alkyl chain having from one to five carbon atoms attached to a carbonyl moiety. Typical $C_2$–$C_6$ alkanoyl groups include ethanoyl, propanoyl, isopropanoyl, butanoyl, t-butanoyl, pentanoyl, hexanoyl, 3-methylpentanoyl and the like.

The term "aryl" represents a phenyl or naphthyl ring which is optionally substituted with halo, hydroxy, or $C_1$–$C_4$ alkoxy.

The term "aryl($C_1$–$C_6$)alkyl" represents a straight or branched alkyl chain having from one to six carbon atoms with an aryl group attached to it. Typical aryl($C_1$–$C_4$)alkyl groups include phenylmethyl, 2-naphth-1-ylethyl, 3-naphth-2-ylpropyl, 2-phenylisopropyl, 4-naphth-1-ylbutyl, 3-phenylpentyl, and the like. The term "aryl($C_1$–$C_6$)alkyl" includes within its definition the term "aryl($C_1$–$C_4$)alkyl."

The term "heterocycle" represents an unsubstituted or substituted stable 5- to 7-membered monocyclic or 7- to 10-membered bicyclic heterocyclic ring which is saturated and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The heterocyclic ring may be attached at any heteroatom or carbon atom which affords a stable structure. The heterocycle is unsubstituted or substituted with 1, 2 or 3 substituents independently selected from halo, hydroxy, halo($C_1$–$C_4$)alkyl, $C_1$–$C_4$ alkyl.

The term "unsaturated heterocycle" represents an unsubstituted or substituted stable 5- to 7-membered monocyclic or 7- to 10-membered bicyclic heterocyclic ring which has one or more double bonds and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quarternized and including a bicyclic group in which any of the above-defined heterocyclic rings is fused to a benzene ring. The unsaturated heterocyclic ring may be attached at any heteroatom or carbon atom which affords a stable structure. The unsaturated heterocycle is unsubstituted or substituted with 1, 2 or 3 substituents independently selected from halo, halo($C_1$–$C_4$)alkyl, hydroxy, $C_1$–$C_4$ alkyl.

Examples of such heterocycles and unsaturated heterocycles include piperidinyl, piperazinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoazolyl, furyl, tetrahydrofuryl, tetrahydropyranyl, thienyl, benzothienyl, thiamorpholinyl, thiamorpholinylsulfoxide, thiamorpholinylsulfone, oxadiazolyl, triazolyl, tetrahydroquinolinyl, tetrahydrisoquinolinyl, 3-methylimidazolyl, 3-ethylpyridyl, 4-chloroquinolinyl, 4-bromothiazolyl, 8-methylquinolinyl, 6-chloroquinoxalinyl, 3-ethylpyridyl, 6-methylbenzimidazolyl, 4-hydroxyfuryl, 4-methylisoquinolinyl, 6,8-dibromoquinolinyl, 4,8-dimethylnaphthyl, 2-methyl-1,2,3,4-tetrahydroisoquinolinyl, N-methylquinolin-2-yl, 2-t-butylcarbonyl-1,2,3,4-isoquinolin-7-yl, 4-methylpiperazinyl, and the like.

"Unsaturated heterocycle($C_1$–$C_4$)alkyl" represents a straight or branched alkyl chain having from one to four carbon atoms with an unsaturated heterocycle group attached to it. Typical unsaturated heterocycle($C_1$–$C_4$)alkyl groups include pyrrolylmethyl, quinolinylmethyl, 1-indolylethyl, 2-furylethyl, 3-thien-2-ylpropyl, 1-imidazolylisopropyl, 4-thiazolylbutyl, and the like.

"Heterocycle($C_1$–$C_4$)alkyl" represents a straight or branched alkyl chain having from one to four carbon atoms with a heterocycle group attached to it. Typical heterocycle ($C_1$–$C_4$)alkyl groups include tetrahydrofurylmethyl, tetrahydropyranylmethyl, 1-indolylethyl, 2-tetrahydrisoquinolinylethyl, 3-tetrahydroquinolinylpropyl, morpholinoisopropyl, 4-piperazinylbutyl and the like.

The term "amino acid side chain" represents the distinctive atom or group bonded to an α-carbon atom also having bonded thereto a carboxyl group and an amino group. These side chains are selected from those found on the following amino acids:

| | |
|---|---|
| Alanine | Ala |
| Arginine | Arg |
| Asparagine | Asn |
| Aspartic acid | Asp |
| Cysteine | Cys |
| Glutamine | Gln |
| Glutamic acid | Glu |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

The term "amino-protecting group" as used in the specification refers to substituents of the amino group commonly employed to block or protect the amino functionality while reacting other functional groups on the compound. Examples of such amino-protecting groups include formyl, trityl, phthalimido, trichloroacetyl, chloroacetyl, bromoacetyl, iodoacetyl; or urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxy-carbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl) ethoxycarbonyl, 2-(methylsulfonyl)ethoxycarbonyl, 2-(triphenylphosphino)ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; or benzoylmethylsulfonyl, 2-nitrophenylsulfenyl, diphenylphosphine oxide and like amino-protecting groups.

The species of amino-protecting group employed is not critical so long as the derivatized amino group is stable to the condition of subsequent reaction(s) on other positions of the intermediate molecule and can be selectively removed at the appropriate point without disrupting the remainder of the molecule including any other amino-protecting group(s). Preferred amino-protecting groups are t-butoxycarbonyl (t-Boc) and benzyloxycarbonyl (CbZ). Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and sons, New York, N.Y., 1981, Chapter 7.

The term "carboxy-protecting group" as used in the specification refers to substituents of the carboxy group commonly employed to block or protect the carboxy functionality while reacting other functional groups on the compound. Examples of such carboxy-protecting groups includes methyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, β-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl and like moieties. A preferred method of protecting the carboxy group involves converting the carboxy moiety to an amide moiety and then hydrolyzing the amide back to provide the desired carboxy substituent. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

The compounds of the present invention have at least five asymmetric centers denoted by an asterisk in the formula below:

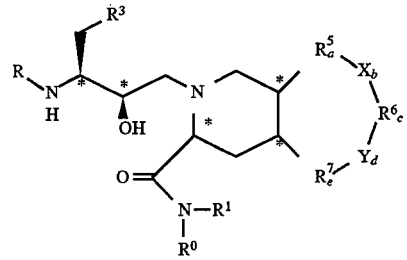

As a consequence of these asymmetric centers, the compounds of the present invention can occur as mixtures of diastereomers, racemic mixtures and as individual enantiomers. All asymmetric forms, individual isomers and combinations thereof, are within the scope of the present invention.

A preferred stereochemistry for compounds of formula (I) includes:

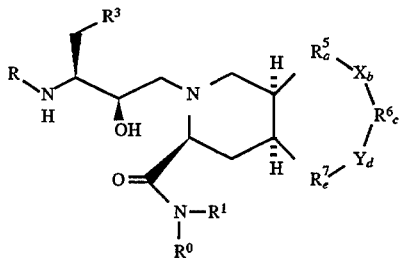

As mentioned above, the invention includes the pharmaceutically acceptable salts of the compounds defined by formula (I). A compound of this invention may possess a sufficiently acidic, a sufficiently basic, or both functional groups, and accordingly react with any of a number of inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like.

Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

Preferred compounds of formula (I) are those compounds of the formula:

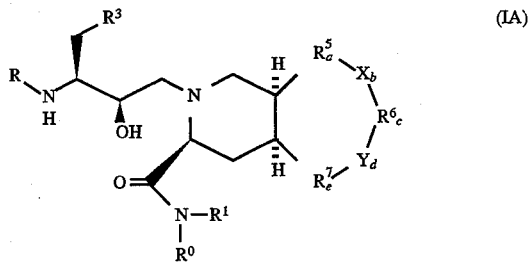

or a pharmaceutically acceptable salt thereof.

Of these preferred compounds, more preferred are the compounds of formula (IA) where:

the sum of a, b, c, d, and e is 3 or 4;
R is a group of the formula:

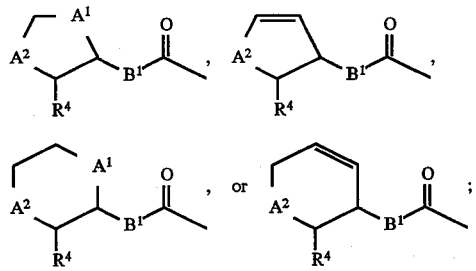

$A^1$ is —C—, —O—, —S—, —S(O)$_2$—;
$A^2$ is —C—, —O—, —S—, or —S(O)$_2$—;
$B^1$ is —O—, —CH$_2$—, or —NH—;
$R^3$ is —(CH$_2$)—$R^{3a}$;
$R^{3a}$ is aryl, or —S-aryl;
$R^0$ and $R^1$ are independently hydrogen, or $C_1$–$C_6$ alkyl;
each of $R^{5x}$, $R^{6x}$, and $R^{7x}$ is independently selected from the group consisting of halo, $C_1$–$C_6$ alkyl, hydroxy($C_1$–$C_4$)alkyl or $C_1$–$C_4$ alkylthio; and
X and Y are independently —S—, —O—, or —NH—;
or a pharmaceutically acceptable salt thereof.

Of these preferred compounds, especially preferred are those compounds where:

one of b and d is 0;

$A^1$ is —C—, —S(O)$_2$—;
$A^2$ is —C—, —O—, —S—, or —S(O)$_2$—; and
$B^1$ is —O—, or —CH$_2$—;

or a pharmaceutically acceptable salt thereof.

The most preferred compounds are N-t-butylocnahydro-5[2R-hydroxy-3R-N(1',1'-dioxo-2'R-isopropyl-tetrahydrothiophen-3'R-yloxycarbonyl)amino-4-phenylthio-)-butyl]-(3aR,7aS)-thieno[3,2-c]pyridine-(6S)-carboxamide;

N-t-butyl-octahydro-5[2R-hydroxy-3R-N(2R-isopropyl-tetrahydrothiophen-3'R-yloxycarbonyl)amino-4-phenylthio)-butyl]-(3aR,7aS)-thieno[3,2-c]pyridine-(6S)-carboxamide;

N-t-butyl-octahydro-5[2R-hydroxy-3R-N(1',1'-dioxo-tetrahydrothiophen-3'R-yloxycarbonyl)amino-4-phenylthio)-butyl]-(3aR,7aS)-thieno[3,2-c]pyridine-(6S)-carboxamide;

N-t-butyl-octahydro-5[2R-hydroxy-3R-N(1',1'-dioxo-tetrahydrothiophen-3'R-ylmethylcarbonyl)amino-4-phenylthiobutyl]-(3aR,7aS)-thieno[3,2-c]pyridine-(6S)-carboxamide;

N-t-butyl-octahydro-5[2R-hydroxy-3R-N(2'S-methyl-tetrahydrothiofuran-3'S-yloxylcarbonyl)amino-4-phenylthio-)-butyl]-(3aR,7aS)-thieno[3,2-c]pyridine-(6S)-carboxamide;

N-t-butyl-octahydro-5[2R-hydroxy-3S-phenylmethyl-4-aza-5-oxo-6S-N(trifluoromethylcarbonyl)amino-7-naphth-2-ylsulfonyl-heptyl]-(3aR,7aS)-thieno[3,2-c]pyridine-(6S)-carboxamide;

N-t-butyl-octahydro-5[2R-hydroxy-3S-phenylmethyl-4-aza-5-oxo-6S-N(trifluoromethylcarbonyl)amino-7-quinolin-8-ylsulfonyl-heptyl]-(3aR,7aS)-thieno[3,2-c]pyridine-(6S)-carboxamide;

N-t-butyl-octahydro-5[2R-hydroxy-3R-N(1',1'-dioxo-2'R-methyl-tetrahydrothiophen-3'R-yloxycarbonyl)amino-4-phenylthio)-butyl]-(3aR,7aS)-thieno[3,2-c]pyridine-(6S)-carboxamide;

N-t-butyl-octahydro-5[2R-hydroxy-3R-N(1',1'-dioxo-2'S-methyl-tetrahydrothiophen-3'S-yloxycarbonyl)amino-4-phenylthio)-butyl]-(3aR,7aS)-thieno[3,2-c]pyridine-(6S)-carboxamide;

N-t-butyl-octahydro-5[2R-hydroxy-3R-N(1',1'-dioxo-2'S-methyl-tetrahydrothiophen-3'S-yloxycarbonyl)amino-4-phenylthio)-butyl]-(3aR,7aS)-thieno[3,2-c]pyridine-(6S)-carboxamide;

N-t-butyl-octahydro-5[2R-hydroxy-3R-N(1',1'-dioxo-2'R-methyl-tetrahydrothiophen-3'R-yloxycarbonyl)amino-4-phenylthio)-butyl]-(3aR,7aS)-thieno[3,2-c]pyridine-(6S)-carboxamide;

or a pharmaceutically acceptable salt of any of the foregoing most preferred compounds.

Examples of pharmaceutically acceptable salts of any of the foregoing most preferred compounds include:

N-t-butyl-octahydro-5[2R-hydroxy-3R-N(1',1'-dioxo-2'S-methyl-tetrahydrothiophen-3'S-yloxycarbonyl)amino-4-phenylthio)-butyl]-(3aR,7aS)-thieno[3,2-c]pyridine-(6S)-carboxamide methanesulfonate; and N-t-butyl-octahydro-5[2R-hydroxy-3R-N(1',1'-dioxo-2'R-methyl-tetrahydrothiophen-3'R-yloxycarbonyl)amino-4-phenylthio)-butyl]-(3aR,7aS)-thieno[3,2-c]pyridine-(6S)-carboxamide methanesulfonate.

The compounds of formula (I) where

R is 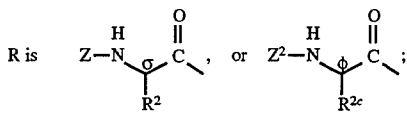

may be prepared by deprotecting a compound of the formula (IA)

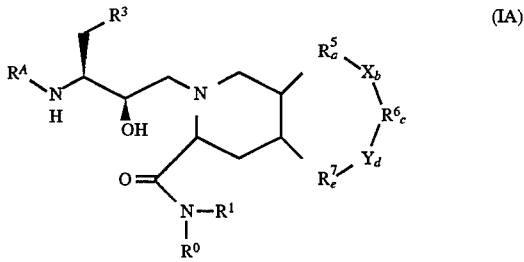

and then reacting the resultant amine with a carboxylic acid reactant of the formula

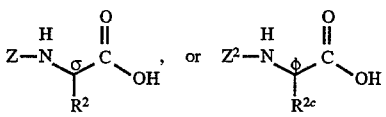

in an aprotic solvent or mixture of solvents. The reaction is carried out in the presence or absence of a promoting agent, preferably in the presence of a promoting agent, and in the presence of a coupling reagent. Typical aprotic solvents for this reaction are tetrahydrofuran and dimethylformamide, or a mixture of such solvents. The reaction is carried out at a temperature from about −30° C. to about 25° C. The amine reactant is generally employed in equimolar proportions relative to the carboxylic acid reactant, in the presence of an equimolar quantity to a slight excess of the coupling reagent. Typical coupling reagents include the carbodiimides such as dicyclohexylcarbodiimide (DCC) and N,N'-diethylcarbodiimide; the imidazoles such as carbonyldiimidazole; as well as reagents such as bis(2-oxo-3-oxazolidinyl) phosphinic chloride (BOP-Ci) or N-ethoxycarbonyl-2-ethoxy-1,2-dihydroquinoline (EEDQ). A preferred coupling reagent for this reaction is DCC. A promoting agent is preferably included for this reaction; a preferred promoting agent is hydroxybenzotriazole hydrate (HOBT·H$_2$O).

Once the reaction is complete, the compound may be isolated, if desired, by procedures known in the art, for example, the compound may be crystallized and then collected by filtration, or the reaction solvent may be removed by extraction, evaporation or decantation. The compound may be further purified, if desired, by common techniques such as crystallization or chromatography over solid supports such as silica gel or alumina.

In addition to the above-described coupling method, the compounds of formula (I), where Z is carbamoyl, formyl, C$_2$–C$_6$ alkanoyl, C$_1$–C$_4$ alkoxycarbonyl or —S(O)$_2$—Z$^1$, where Z$^1$ is as defined above for formula (I) may be prepared by deprotecting a compound of formula (IA), and then reacting the resultant amine with an amino-protected compound having the formula, R$^4$—NH—C(σ)H(R$^2$)—COOH or R$^4$—NH—C(φ)H(R$^{2c}$)—COOH where R$^4$ is an amino-protecting group.

The amino-protecting group is then removed from the resulting compound according to procedures and methods known in the art to provide the compound of formula (I), where Z or Z$^2$ is hydrogen. The resulting compound is then acylated or sulfonylated using procedures known in the art. For example, the amine compounds may be acylated by reaction with a suitable acyl halide, isocyanate or chloroformate, preferably in the presence of an acid scavenger such as a tertiary amine, preferably triethylamine. The reaction is carried out at a temperature of from about −20° C. to about 25° C. Typical solvents for this reaction include ethers and chlorinated hydrocarbons, preferably diethylether, chloroform or methylene chloride. The amine compounds may be sulfonylated by reaction with a suitably substituted sulfonyl halide of the formula, Z$^1$—SO$_2$-halide in an aprotic solvent at a temperature from about −30° C. to about 25° C. in an aprotic solvent such as tetrahydrofuran. The amine reactant is generally employed in equimolar proportions relative to the sulfonyl halide reactant, and preferably in the presence of an acyl transfer catalyst. A preferred acyl transfer catalyst for this reaction is N-methylmorpholine (NMM).

Compounds of formula (I), wherein R$^2$ is —(CH$_2$)$_y$—W—R$^{2a}$, where y and R$^{2a}$ are as defined above; and W is —C(O)—NR$^{2b}$—, can be prepared by deprotecting a compound of formula (IA), and then reacting the resultant amine with an amino-protected and carboxy-protected compound having the formula:

where R$^{2z}$ is a carboxy-protecting group.

The carboxy-protecting group is then removed and the resultant compound is reacted with a suitably substituted amine reactant of the formula, H—NR$^{2a}$R$^{2b}$, substantially in accordance with the procedure detailed in Reaction I. A preferred solvent for this reaction is a mixture of tetrahydrofuran and dimethylformamide. A preferred coupling reagent for this reaction is DCC. A preferred promoting agent is HOBT·H$_2$O. The amino-protecting group is then removed from the resultant compound according to procedures and methods known in the art to provide a compound of formula (I) where Z is hydrogen, which can then be acylated or sulfonylated using procedures known in the art. For example, the amine compounds may be acylated by reaction with a suitable acyl halide, isocyanate or chloroformate, preferably in the presence of an acid scavenger such as a tertiary amine, preferably triethylamine. The reaction is carried out at a temperature of from about −20° C. to about 25° C. Typical solvents for this reaction include ethers and chlorinated hydrocarbons, preferably diethyl ether, chloroform or methylene chloride. The amine compounds may be sulfonylated by reaction with a suitably substituted sulfonyl halide of the formula, Z$^1$—SO$_2$-halide as described above.

Further, a compound of formula (I), wherein R$^2$ is —(CH$_2$)$_y$—W—R$^{2a}$, where y and R$^{2a}$ are as defined above; and W is —S(O)— or —S(O)$_2$— may be prepared by oxidizing an intermediate compound of formula IB

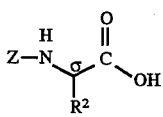

where:
R$^2$ is —(CH$_2$)$_y$—W—R$^{2a}$, where y, Z and $R^{2a}$ are as defined above; and W is —S—;

under standard reaction conditions known in the art. For example, the intermediate compound using X is —S— may be combined with an oxidizing agent in an aqueous or organic solvent at a temperature of from about −78° C. to 25° C. Solvent choice is not critical so long as the solvent employed is inert to the ongoing reaction and the reactants are sufficiently solubilized to effect the desired reaction. Typical oxidizing agents include oxone®, m-chloroperoxybenzoic acid. A preferred oxidizing agent is oxone®.

Compounds of formula (I) wherein R is a group of the formula:

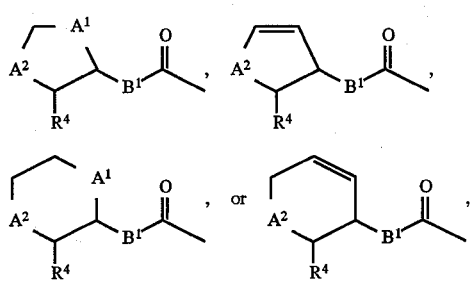

$A^1$, $A^2$, and $R^4$ are as defined above for formula (I); and $B^1$ is —CH$_2$— or —CH$_2$CH$_2$— may be prepared by deprotecting a compound of formula (IA), and then acylating the resultant amine with a carboxylic acid reactant of the formula:

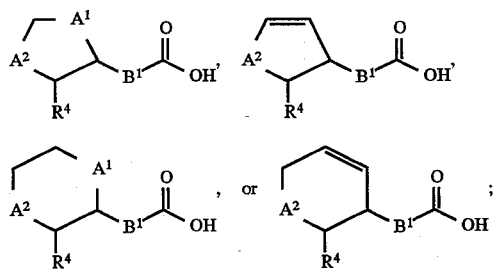

in an aprotic solvent or mixture of solvents. The reaction is carried out in the presence or absence of a promoting agent, preferably in the presence of a promoting agent, and the presence of a coupling reagent. Typical aprotic solvents for this reaction are tetrahydrofuran and dimethylformamide, or a mixture of such solvents. The reaction is carried out at a temperature from about −30° C. to about 25° C. The amine reactant is generally employed in equimolar proportions relative to the carboxylic acid reactant, in the presence of an equimolar quantity to a slight excess of the coupling reagent. Typical coupling reagents include the carbodiimides such as dicyclohexylcarbodiimide (DCC) and N,N'-diethylcarbodiimide; the imidazoles such as carbonyldiimidazole; as well as reagents such as bis(2-oxo-3-oxazolidinyl) phosphinic chloride (BOP-Cl) or N-ethoxycarbonyl-2-ethoxy-1,2-dihydroquinoline (EEDQ). A preferred coupling reagent for this reaction is DCC. A promoting agent is preferably included for this reaction; a preferred promoting agent is hydroxybenzotriazole hydrate (HOBT·H$_2$O).

Compounds of formula (I) wherein R is a group of the formula:

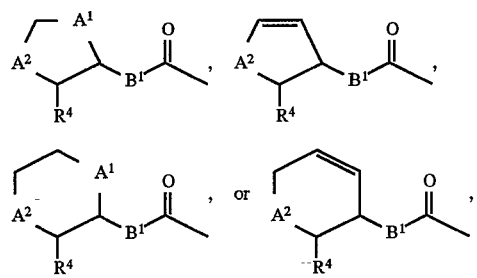

$A^1$, $A^2$, and $R^4$ are as defined above for formula (I); and $B^1$ is —O—, —S—, —NH—, or —N(CH$_3$)—;

may be prepared by activating an appropriately substituted compound of the formula:

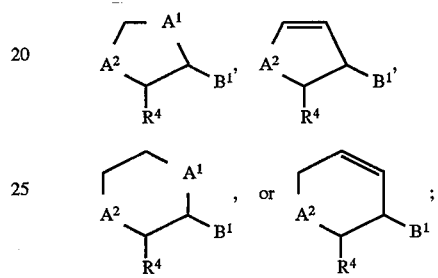

to form a coupling reagent (specifically, an activated carbonate ($B^1$ is —O—), an activated carbamate (where $B^1$ is —N— or —N(CH$_3$)—) and an activated thiocarbonate (where $B^1$ is —S—)).

The coupling reagent is then reacted with an amine reactant (obtained by deprotecting a compound of formula (IA)), preferably in the presence of an acid scavenger such as a tertiary amine, preferably triethylamine. The reaction is carried out at a temperature of from about −20° C. to about 25° C. Typical solvents for this reaction include ethers and chlorinated hydrocarbons, preferably diethylether, chloroform or methylene chloride.

In addition, compounds of formula (I) wherein R is a compound of the formula:

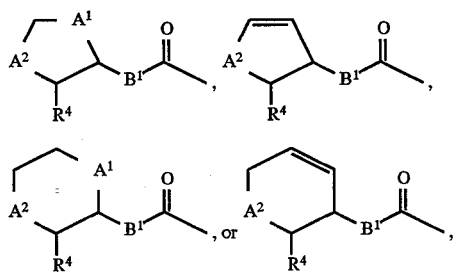

$A^1$, $A^2$, and $R^4$ are as defined above for formula (I); and $B^1$ is —NH—;

may be prepared by reacting an appropriately substituted amino compound of the formula:

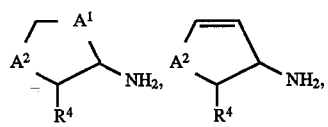

-continued

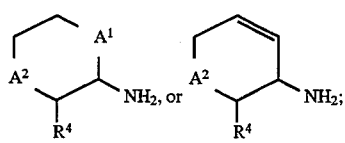

to provide an isocyanate reactant.

For example, the amino reactant may be reacted with triphosgene in a mutual inert solvent. The reactants are generally employed in an amount ranging from about equimolar proportions to about a two molar excess, preferably in about a one molar excess relative to the triphosgene. A base, for example a trialkylamine such as triethylamine or diisopropylethylamine and the like, may be added to promote the raction. Typical solvents suitable for use in this reaction include any organic solvent such as toluene. Solvent choice is not critical so long as the solvent employed is inert to the ongoing reaction and the reactants are sufficiently solubilized to effect the desired reaction. The reaction is generally substantially complete after about 6 to 24 hours when conducted at a temperature in the range of from about 25° C. to the reflux temperature of the reaction mixture. The reaction is preferably conducted at a temperature in the range of from about 80° C. to the reflux temperature of the reaction mixture for about 8 hours to 12 hours.

The isocyanate compound is then reacted with a deprotected amino compound of formula (IA) in a mutual inert solvent. Better results may be obtained by catalysis with copper salts, for example copper (I) iodide or copper (I) chloride. The isocyanate compound is generally employed in an amount ranging from about equimolar proportions to about a one molar excess. Typical solvents suitable for use in this reaction include any organic solvent such as dimethylformamide. Solvent choice is not critical so long as the solvent employed is inert to the ongoing reaction and the reactants are sufficiently solubilized to effect the desired reaction. The reaction is generally substantially complete after about 15 minutes to 3 hours when conducted at a temperature in the range of from about 10° C. to about 40° C. The reaction is preferably conducted at a temperature in the range of from about 15° C. to about 30° C. for about 15 minutes to 2 hours.

Compounds of formula (IA) may be prepared according to the procedures shown in Reaction Scheme I.

Reaction Scheme I

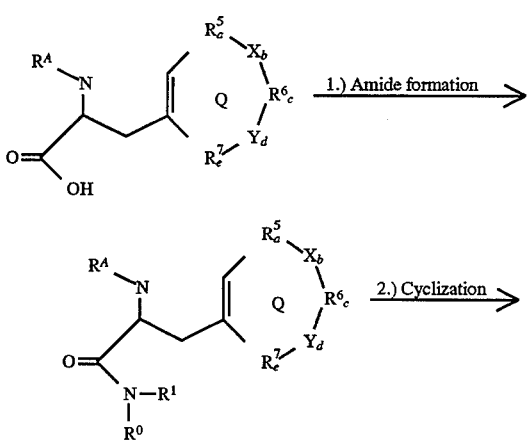

-continued
Reaction Scheme I

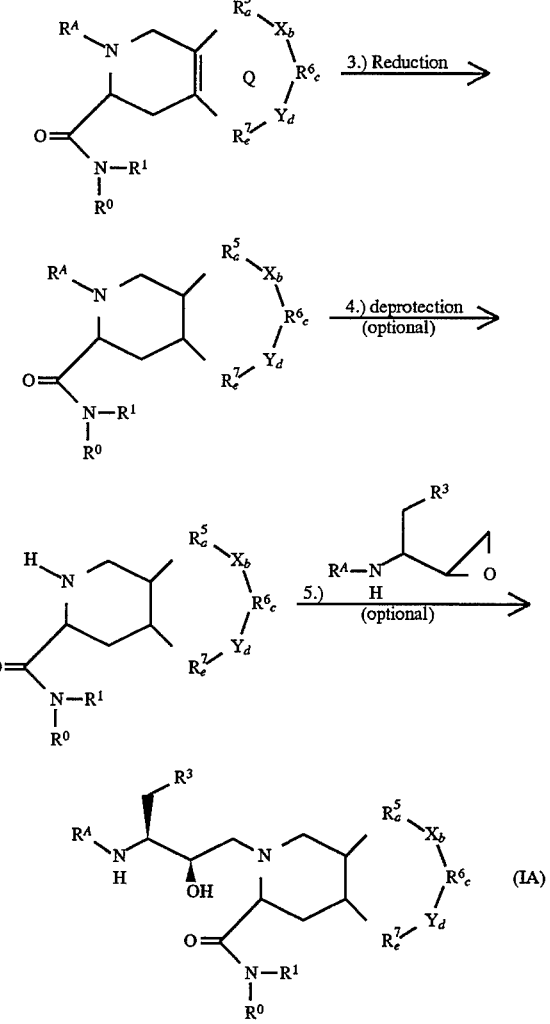

where:
R⁴, R³, R⁰, R¹, R⁵, X, R⁶, Y, R⁷ a, b, c, d, and e are as defined above for formula (I);

R⁴ is an amino-protecting group; and

Q on the bicyclic ring in reaction 1–3, above, represents the presence of double bonds between, for example, $R_a$ and $R_c$, $R_a$ and $R_d$, or $R_e$ and $R_c$ and the like, where b, b or d is 0, respectively.

Reaction Scheme I, above, is accomplished by carrying out reactions 1–3 (or 1–5) in sequential order. Once a reaction is complete, the intermediate compound may be isolated, if desired by procedures known in the art, for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

Reaction I.1 is typically carried out by activating the carboxylic acid moiety using, for example, DCC, or a mixed anhydride such as isobutyl, followed by reaction with a primary or secondary amine having the formula NR⁰R¹ where R⁰ and R¹ are as defined above for formula (I). The reaction is typically carried out in a nonpolar aprotic solvent or mixture of solvents in the presence or absence of an acid scavenger at a temperature of from about −20° C. to about 25° C. to afford the corresponding amide. Suitable solvents for this reaction include ethers and chlorinated hydrocarbons, preferably diethyl ether, trichloroethane, or methylene chloride. Preferably, this reaction is preferably carried out in the presence of an acid scavenger such as a tertiary amine, preferably triethylamine. The amide afforded by this reaction may be isolated or further reacted as shown in Reaction 2.

Reaction I.2 is typically carried out by reacting the compound obtained from Reaction I.1 using the procedures detailed in *Comprehensive Organic Synthesis*, "Heteroatom Manipulation", Barry M. Trost, ed., volume 6, pages 736–746, (1991). In general, an appropriately substituted monocyclic ring is reacted with an aldehyde, such as formaldehyde or trichloroacetaldehyde in the presence of an acid. The acid may be used as a solvent. Typical acids include hydrochloric acid, hydrobromic acid, sulfuric acid, acetic acid, trifluoroacetic acid, and the like. A co-solvent may optionally be added to the reaction mixture. The co-solvent choice is not critical so long as the co-solvent employed is inert to the ongoing reaction and the reactants are sufficiently solubilized to effect the desired reaction. Typical solvents for this reaction include halogenated solvents such as methylene chloride, trichloroethane, carbontetrachloride, and the like. Alternatively, an aldehyde equivalent may be used, for example, dimethoxymethane and a suitable acid.

In reaction I.3, the compound isolated from reaction I.2 is reduced to provide a saturated heterocyclic compound as depicted above. Catalytic hydrogenation is a preferred method of reduction. Typical catalysts include palladium catalysts, rhodium catalysts (for example rhodium on alumina), rhenium catalysts and the like. Preferred catalysts include palladium-on-carbon. Suitable solvents for this reaction include the $C_1$–$C_4$ alcohols, tetrahydrofuran, acetic acid in alcohol, ethyl acetate and the like. A preferred solvent is ethanol. The reaction is typically carried out under an atmosphere of hydrogen from about 500 to about 4000 psi at a temperature of from about 25° C. to about 150° C. Preferably, the reaction is carried out under an atmosphere of hydrogen from about 2000 to about 3000 psi at a temperature of from about 50° C. to 100° C. The catalyst is generally employed in an amount ranging from about equivalent proportions to about a twelve-fold excess (by weight) of the reactant, preferably in about a six- to ten-fold excess (by weight) of the catalyst relative to the substrate.

Reactions I.4 and I.5 may be used to prepare compounds of formula (I) where

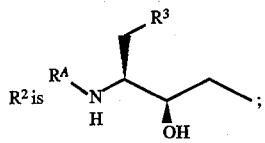

$R^3$ and $R^4$ are as defined above.

Reaction I.4 is a standard amino deprotection reaction using procedures and methods known in the art to afford the corresponding amine which is then used in Reaction I.5, above. Chemical deprotection procedures are preferred. For example, the compound isolated from I.3 may be deprotected using trimethylsilyliodide (TMSI) in an aprotic solvent or mixture of solvents at a temperature of from about 10° C. to 60° C., preferably at a temperature of from about 20° C. to 40° C. Typical solvents include methylene chloride, acetonitrile, trichloroethane, and the like.

In reaction I.5, the epoxide prepared in Reaction A.5, below, is reacted with compound isolated from Reaction I.4 in an alcoholic solvent at a temperature of from about 20° C. to 100° C. Solvent choice is not critical so long as the solvent employed is inert to the ongoing reaction and the reactants are sufficiently solubilized to effect the desired reaction. Typical solvents for this reaction include the alcohols, preferably isopropanol or ethanol. The reaction is preferably carried out at a temperature of about 65° C.

The compound of formula (IA), isolated from reaction I.5, may be deprotected and then coupled or reacted as described above to provide a compound of formula (I).

The epoxide used in Reaction I.5 may be synthesized using Reaction Scheme A.

Reaction Scheme A

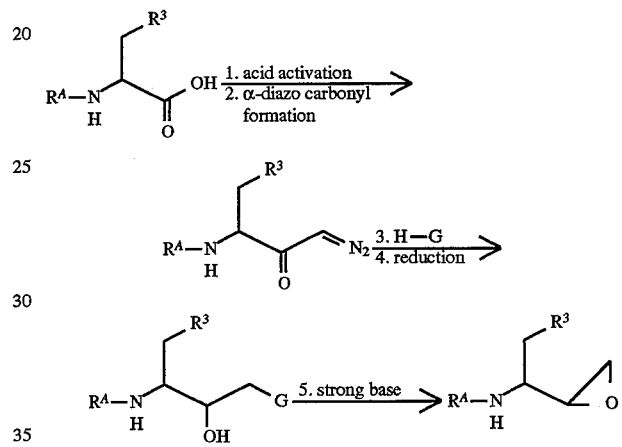

where:
$R^4$ is an amino-protecting group;
$R^3$ is as defined above for formula (I); and
G is halo.

Reaction Scheme A, above, is accomplished by carrying out reactions 1–5 in sequential order. Once a reaction is complete, the intermediate compound may be isolated, if desired by procedures known in the art, for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

Reaction A.1 is carried out by activating, that is, converting, an amino-protected carboxylic acid reactant having the structure:

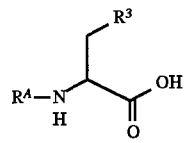

to the corresponding mixed anhydride under conditions known in the art. For example, the amino-protected carboxylic acid reactant may be reacted with a $C_1$–$C_6$ alkylchloroformate, such as isobutylchloroformate preferably in the presence of an acid scavenger. Preferred acid scavengers are the trialkylamines, preferably triethylamine. The reaction is typically carried out in an aprotic solvent such as ethyl acetate. Solvent choice is not critical so long as the solvent employed is inert to the ongoing reaction and the reactants are sufficiently solubilized to effect the desired reaction. The resulting mixed anhydride reactant is preferably used in Reaction A.2 without further isolation or purification.

Reaction A.2 is accomplished in two steps. First, a solution of sodium hydroxide, covered with a layer of an ether solvent, preferably diethyl ether, is reacted with a large excess of N-methyl-N-nitro-N-nitrosoguanidine to form a diazomethane reactant. The sodium hydroxide is preferably used as an aqueous solution having about four to six mol/liter of sodium hydroxide. Once this reaction is substantially complete, the organic layer is dried over a dessicant such as potassium hydroxide. This solution is then reacted with the mixed anhydride from Reaction A.1. above, to form the corresponding α-diazo carbonyl compound. The diazomethane reactant is preferably used in this reaction without isolation or purification. The reaction is typically carried out at a temperature of from about −50° C. to about −10° C., preferably about −20° C.

In Reaction A.3, the α-diazo carbonyl compound prepared in Reaction A.2 is reacted with an acid of the formula H-G where G is halo, in an aprotic solvent such as diethylether to form an α-halo carbonyl compound. A preferred acid reactant is hydrochloric acid which provides the corresponding α-chloro carbonyl compound. The reaction is typically carried out at a temperature from about −30° C. to about 0° C. Solvent choice is not critical so long as the solvent employed is inert to the ongoing reaction and the reactants are sufficiently solubilized to effect the desired reaction. The acid reactant is typically added in the form of an anhydrous gas in small increments until the reaction appears substantially complete. The reaction can be monitored by thin layer chromatography.

In Reaction A.4, the carbonyl moiety on the compound prepared in Reaction A.3 is reduced using standard conditions known in the art to form the corresponding α-chloro hydroxy compound. For example, the compound prepared in Reaction A.3 is combined with a reducing agent in a mixture of solvents. Typical reducing agents include sodium borohydride, lithium borohydride, zinc borohydride, diisobutylaluminum hydride, and sodium bis(2-methoxyethoxy)aluminum hydride. A preferred reducing agent is sodium borohydride. Typical solvent mixtures include a protic and aprotic mixture such as tetrahydrofuran/water. Solvent choice is not critical so long as the solvent employed is inert to the ongoing reaction and the reactants are sufficiently solubilized to effect the desired reaction. The reaction is typically carried out at a temperature from about −10° C. to about 10° C., preferably about 0° C.

In Reaction A.5, the α-chloro hydroxy compound prepared in Reaction A.4 is treated with a strong base to form the corresponding epoxide (which is used above in Reaction I.5) under standard conditions known in the art. For example, the α-chloro hydroxy compound may be reacted with a potassium hydroxide/ethanol mixture in an alcoholic solvent such as ethanol. The reaction is typically carried out at a temperature from about 0° C. to about the reflux temperature of the solvent. Preferably the reaction is carried out at room temperature.

The compounds of formula IA, where $R^3$ is —O—$R^{3a}$ or —S—$R^{3a}$ are prepared with an amino-protected amino acid reactant having the following structure:

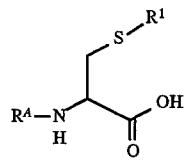

where $R^3$ and $R^4$ are as defined above.

These compounds may be prepared substantially in accordance with the reaction scheme described in Vederas et al., J. Am. Chem. Soc., 107, 7105–7109 (1985). In particular, this reaction scheme is carried out by first reacting amino-protected serine with triphenylphosphine, dimethylazodicarboxylate (DMAD) or diethylazodicarboxylate (DEAD) in an aprotic solvent at a temperature of from about −80° C. to 0° C. to form the corresponding β-lactone. The reaction is typically carried out in an ether, such as tetrahydrofuran at a temperature of from about −80° C. to −50° C. Next, the lactone ring is opened with an appropriately substituted thio anion, —S—$R^{3a}$, where $R^{3a}$ is as defined above. The thio anion compound is preferably formed by reacting the corresponding thiol with a strong base, such as sodium hydride or potassium hydride. This reaction is typically carried out in an aprotic solvent at a temperature from about 0° C. to about 40° C. and under an inert atmosphere, such as nitrogen. Typical solvents for this reaction include ethers, preferably tetrahydrofuran.

Alternatively, the compounds of formula IA, where $R^3$ is —S-aryl, may be prepared using the procedures detailed in Photaki, J. Am. Chem. Soc., 85, 1123 (1963), and Sasaki, N. A. et al, Tetrahedron Letters, 28, 6069 (1987). For example, the compounds may be prepared by reacting doubly protected serine (carboxy-protected and amino-protected) with toluenesulfonyl chloride in the presence of dimethylaminopyridine (DMAP) and an acid scavenger such as pyridine in an aprotic solvent such as methylene chloride to form the corresponding toluenesulfonate which may then be reacted with an appropriately substituted thioanion having the structure, —S-aryl. The thioanion compound is preferably formed by reacting the corresponding thiol with a strong base as described above. The carboxy-protecting group may be removed from the resulting doubly protected arylthioalanine using conditions known in the art.

It will be understood by those skilled in the art that in performing the processes described above it may be desirable to introduce chemical protecting groups into the reactants in order to prevent secondary reactions from uaking place. Any amine, alkylamine or carboxy groups which may be present on the reactants may be protected using any standard amino- or carboxy-protecting group which does not adversely affect the remainder of the molecule's ability to react in the manner desired. The various protective groups may be removed simultaneously or successively using methods known in the art.

As noted above, all asymmetric forms, individual isomers and combinations thereof are considered part of this invention. Such isomers may be prepared from their respective precursors by the procedures described above, by resolving the racemic mixtures or by separating diastereomers. The resolution can be carried out in the presence of a resolving agent, by chromatography, or by repeated crystallization or by some combination of these techniques which are known in the art. Further details regarding resolutions can be found in Jacques et al., Enantiomers, Racemates, and Resolutions, John Wiley & Sons 1981.

It is recognized that various isomers, and combinations of isomers may be prepared using the procedures disclosed in the present application due to the number of asymmetric centers in the claimed compounds. Both the diastereomeric and enantiomeric purity of the reactants will affect the number of isomers in the final product. It is understood by persons in the art that the isomers may be separated at various steps in the synthesis.

For example, there are a number of isomers that result from acylating a compound of the formula

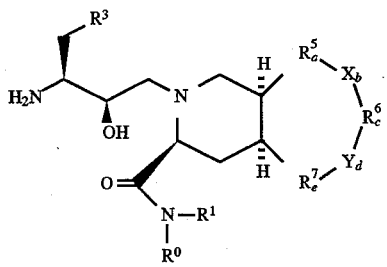

with a carboxylic acid reagent of the formula

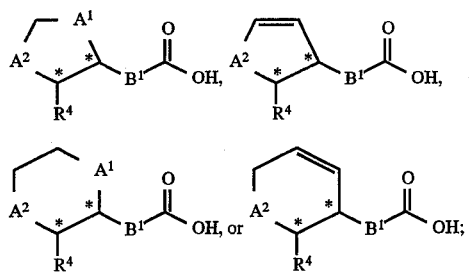

as described above. For example, in the structures depicted above, there are four isomers corresponding to each carboxylic acid reagent (two cis enantiomers and two trans enantiomers). If the carboxylic acid reactant is used without first separating the isomers, then the acylation reaction will result in four diastereomers of the compound of formula I (corresponding to the isomers of the carboxylic reagent). The various isomeric forms of the final product may then be separated according to procedures known in the art, as described above. It is understood by persons in the art that separating diastereomers is difficult to accomplish quantitatively. The various diastereomeric forms of these compounds may be isolated in amounts greater than or equal to 96%, preferably greater than or equal to 98%.

Alternatively, the isomers of the carboxylic acid reactant may be separated and the individual reactants then reacted with the amine compound as described above. The various diastereomeric forms of the carboxylic acid reactants may be separated to provide a pair of enantiomers (cis and trans) each of which may then be separated to provide the individual carboxylic acid reactant in an amount greater than or equal to 85%, preferably greater than or equal to 90% ee.

For example, the enantiomeric forms of the carboxylic acid reagent may be isolated using enzymatic resolution. For example, carboxylic acid reagents where $B^1$ is —O—, may be obtained by enzymatic resolution of an hydroxy-substituted heterocyclic compound which is then converted to the desired carboxylic acid reactant. Typically, the cis and trans forms of hydroxy-substituted heterocyclic compound are first separated using chromatographic means according to procedures known in the art. The individual cis and trans enantiomers may then be isolated, respectively, using enzymatic resolution.

For example, the cis enantiomers of the hydroxy-substituted heterocyclic compound may be reacted with acetic anhydride in the presence of a base such as DMAP to provide the corresponding acetate-substituted heterocyclic compound. This R,R acetate is then selectively hydrolyzed using a catalytic amount of lipase (for example, lipase PS-800, *Pseudomonas fluorescens*, Fluka) in the presence of a surfactant such as Triton® X-100 in a buffered solution (pH 6–8, preferably pH 7) to provide the R,R hydroxy-substituted heterocyclic compound. The absolute stereochemistry may be confirmed by comparison with known compounds.

The remaining S,S acetate-substituted heterocyclic compound may be hydrolyzed using procedures known in the art to provide the desired S,S hydroxy-substituted heterocyclic compound. Alternately, the cis enantiomers of the hydroxy-substituted heterocyclic compound may be reacted with vinyl acetate in the presence of lipase SAM II, (*Pseudomonas fluorescens*, Fluka) to provide a mixture of the R,R acetate-substituted heterocyclic compound and the S,S hydroxy-substituted heterocyclic compound which may then be separated using skills known in the art.

As noted above, these hydroxy compounds may be activated to form a coupling reagent (i.e., an activated carbonate) which is then reacted with an amine reactant (obtained by deprotecting a compound of formula (IA)) to provide the corresponding diastereomer (compound of formula (I)).

The absolute stereochemistry of the compound of formula (I) obtained using enantiomerically pure reactants may then be used to assist in the identification of the various diastereomers isolated from the reaction described above where the enantiomers were not separated before reaction.

The compounds employed as initial starting material in the synthesis of the compounds of this invention are known, and to the extent not commercially available are readily synthesized by standard procedures commonly employed by those in the art.

The pharmaceutically acceptable salts of the invention are typically formed by reacting a compound of formula (I) with an equimolar or excess amount of acid or base. The reactants are generally combined in a mutual solvent such as diethyl ether or benzene, for acid addition salts, or water or alcohols for base addition salts. The salts normally precipitate out of solution within about one hour to about ten days and can be isolated by filtration or other conventional methods.

The following Preparations and Examples further illustrate specific aspects of the present invention. It is to be understood, however, that these examples are included for illustrative purposes only and are not intended to limit the scope of the invention in any respect and should not be so construed.

In the following Preparations and Examples, the terms melting point, nuclear magnetic resonance spectra, electron impact mass spectra, field desorption mass spectra, fast atom bombardment mass spectra, infrared spectra, ultraviolet spectra, elemental analysis, high performance liquid chromatography, and thin layer chromatography are abbreviated "m.p.", "NMR", "EIMS", "MS(FD)", "MS(FAB)", "IR", "UV", "Analysis", "HPLC", and "TLC", respectively. In addition, the absorption maxima listed for the IR spectra are only those of interest and not all of the maxima observed.

In conjunction with the NMR spectra, the following abbreviations are used: "s" is singlet, "d" is doublet, "dd" is doublet of doublets, "t" is triplet, "q" is quartet, "m" is multipier, "dm" is a doublet of multiples and "br.s", "br.d", "br.t", and "br.m" are broad singlet, doublet, triplet, and multiplet respectively. "J" indicates the coupling constant in Hertz (Hz). Unless otherwise noted, NMR data refers to the free base of the subject compound.

The NMR spectra were obtained on a Bruker Corp. 270 MHz instrument or on a General Electric QE-300 300 MHz instrument. The chemical shifts are expressed in delta (δ) values (parts per million downfield from tetramethylsilane). MS(FD) spectra were taken on a Varian-MAT 731 Spectrometer using carbon dendrite emitters. EIMS spectra were obtained on a CEC 21-110 instrument from Consolidated Electrodynamics Corporation. MS(FAB) spectra were obtained on a VG ZAB-3 Spectrometer. IR spectra were obtained on a Perkin-Elmer 281 instrument. UV spectra were obtained on a Cary 118 instrument. TLC was carried out on E. Merck silica gel plates. Melting points are uncorrected.

EXAMPLE 1

N-(Benzyloxycarbony)β-thienyl-L-alanine

A. (Z)-2-Methyl-4-thienylidene-5(4H)-oxazolone

A mixture of 70.6 g (602 mmol) of N-acetylglycine, 100 g (892 mmol) of 2-thiophene-carboxaldehyde (Aldrich), 142.3 mL (154 g, 1.51 mol) of acetic anhydride, and 36.6 g (446 mmol) of sodium acetate was heated on a steam bath for approximately one hour. The resultant reaction mixture was cooled to room temperature and then placed in a refrigerator overnight to provide a solid. This solid was suspended in 250 mL of cold water and then filtered through a Büchner funnel and washed with cold water. The resultant solid was reduced to dryness under reduced pressure to provide 65 g of the desired compound (56%).

B. (Z)-2-Acetamido-3-(2-thienyl)-propenoic acid

A solution of 65 g of the subtitled compound of Example 1A in 240 mL of water and 620 mL of acetone was heated to reflux for approximately four hours. The resulting reaction mixture was cooled and then concentrated under reduced pressure to provide a solid. This solid was redissolved in 100 mL of water and 250 mL of methanol (heated to reflux to dissolve most of the solid) and then filtered hot. The filtrate was cooled resulting in the formation of crystals which were collected by filtration through a Büchner funnel, washed with water and reduced to dryness under reduced pressure to provide 55 g of the titled compound. This compound was used without further purification.

C. (S)-2-Acetamido-3-(thien-2-yl)-propanoic acid

A preformed catalyst was formed by adding 3.92 g of (+)-2,3-O-isopropylidene-2,3-dihydroxy-1,4-bis (diphenylphosphine)butane to 1.76 g of chloro(1,5-cyclooctadiene)rhodium I dimer in 800 mL of toluene, under argon. The resultant mixture was stirred under argon for approximately twenty minutes. Meanwhile, 152 g (720 mmol) of the subtitled compound of Example 1B in 2500 mL of ethanol was shaken under 20 psi of hydrogen gas in a hydrogenation vessel for approximately twenty minutes. The preformed catalyst was then added the hydrogenation vessel, under nitrogen. The resultant reaction mixture was allowed to react at 50° C., under twenty psi of hydrogen gas for approximately sixteen hours. The reaction mixture was concentrated under reduced pressure to provide a brown solid which was treated with 700 mL of water containing 100 g of potassium carbonate. The resultant mixture was filtered through celite, washed with water and the filtrate was combined with diethyl ether. The resultant layers were separated and the aqueous layer was acidified with 5N hydrochloric acid, layered with 1000 mL of methylene chloride. The organic layer was then dried over sodium sulfate, filtered and concentrated to provide a tan solid which was purified by recrystallization from 900 mL of hot ethyl acetate to provide 109 g of the desired subtitled compound (71%).

D. N-Benzyloxycarbonyl-β-thienyl-L-alanine

A solution of 9.03 g (42.4 mmol) of the subtitled compound from Example 1C in 100 mL of 5N hydrochloric acid was heated to reflux for 2 hours. The resultant reaction mixture was cooled to 0° C. and made basic by adding 100 mL of a solution of 3.6M potassium carbonate. To this mixture was then added 150 mL of dioxane followed by 6.0 mL (42.4 mmol) of carbobenzyloxychloride in dioxane. When the reaction is substantially complete, as indicated by TLC (42/7/7/9, ethyl acetate/acetonitrile/water/acetic acid), the reaction mixture was concentrated, then washed with 100 mL of diethyl ether. The resultant layers were separated and the aqueous layer was acidified to pH<2 with 5N hydrochloric acid and extracted with methylene chloride which was then dried with sodium sulfate, filtered and concentrated under reduced pressure to provide 10.85 g of the titled compound.

Yield: 84%.

$[\alpha]_D$ (CDCl$_3$)=37.2° (at 22° C.).

$^1$H NMR (300 MHz, CDCl$_3$): δ7.37 (m, 5H); 7.18 (d, J=4 Hz, 1H); 6.95 (m, 1H); 6.83 (m, 1H); 5.35 (d, J=8 Hz, 1H); 5.15 (s, 2H); 4.7 (m, 1H); and 3.4 (m, 2H).

EXAMPLE 2

N-(Benzyloxycarbonyl) β-thienl-D,L-alanine

To a mixture of 3.0 g (16.9 mmol) of β-thienyl-D,L-alanine in 75 mL of water and 60 mL of dioxane, was added 5.6 g (40.6 mmol) of anhydrous potassium carbonate, followed by 2.85 mL (20 mmol) of carbobenzyloxychloride. The resulting mixture was stirred rapidly for approximately one hour. When the reaction was substantially complete, as indicated by thin layer chromatography (21/7/7/9, ethyl acetate/acetic acid/acetonitrile/water), the reaction mixture was concentrated. The resultant layers were separated and the aqueous layer was washed with 75 mL of diethyl ether and then layered with 150 mL of methylene chloride. The resultant mixture was acidified with rapid stirring to pH=2.0 using 5N hydrochloric acid. The layers were then separated, and the organic layer was dried with sodium sulfate (Na$_2$SO$_4$), filtered and concentrated to provide 5.05 g of desired compound (98%).

$^1$H NMR (300 MHz, CDCl$_3$): δ7.37 (m, 5H); 7.18 (d, J=4 Hz, 1H); 6.95 (m, 1H); 6.83 (m, 1H); 5.35 (d, J=8 Hz, 1H); 5.15 (s, 2H); 4.7 (m, 1H); and 3.4 (m, 2H).

EXAMPLE 3

N-t-Butyl-octahydro-(3aR,7aS)-thieno[3,2-c] pyridine-(6S)-carboxamide

A. N-Benzyloxycarbonyl-β-thienyl-L-alanine-t-butylamide

To a cold (0° C.) mixture of 8.06 g (26.4 mmol) of the subtitled compound of Example 1D in 120 mL of tetrahydrofuran, was added 4.23 mL of N-methylmorpholine followed by the slow addition of 4.04 mL of isobutylchloroformate, and, after approximately fifteen minutes, 3.74 mL of t-butylamine. The resulting reaction mixture was warmed to room temperature, reacted for approximately two hours and then concentrated under reduced pressure to provide a residue. This residue was redissolved in ethyl acetate, and washed sequentially with water, a 1N solution of hydrochloric acid, and a saturated sodium bicarbonate solution. The combined organic portions was dried with sodium sulfate, filtered and concentrated to an oil. This oil was recrystallized from 100 mL of hot hexane to provide an oil which solidified on standing and was then dried to provide 9.25 g of solid (97%).

$^1$H NMR (300 MHz, CDCl$_3$): δ7.37 (s, 5H); 7.2 (d, J=4 Hz, 1H); 6.95 (dd, J=4 Hz, 8 Hz, 1H); 6.87 (d, J=4 Hz, 1H); 5.52 (m, 2H); 5.12 (s, 2H); 4.27 (m, 1H); 3.27 (m, 2H), and 1.23 (s, 9H).

B. N-t-Butyl-5-benzyloxycarbonyl-(4,5,6,7)-tetrahydrothieno[3,2-c]pyridine-(6S)-carboxamide To a solution of 500 mg (1.39 mmol) of the subtitled compound of Example 3A in 12 mL of 1,1,2-trichloroethane, was added 2 mL if trifluoroacetic acid, followed by 2 mL of dimethoxymethane. The resultant reaction mixture was refluxed for approximately fifteen minutes. When the reaction was substantially complete, as indicated by TLC, the reaction mixture was poured into a mixture of 3.5 g of potassium carbonate in 30 mL of water and 40 mL of methylene chloride. The resultant layers were separated, and the organic layer was dried with sodium sulfate, filtered and concentrated under reduced pressure to provide an oil. This oil was purified using flash chromatography (SiO$_2$; eluent of 3% ethyl acetate in methylene chloride) to provide 357 mg of the desired compound (69%).

$^1$H NMR (300 MHz, d$_6$ DMSO): δ7.35 (m, 7H); 6.83 (m, 1H); 5.15 (m, 2H); 4.98 (m, 1H); 4.35 (m, 2H); 3.10 (m, 2H); and 1.10 (s, 9H).

MS: m/e 372 (M$^+$)

C. N-t-Butyl-5-benzyloxycarbonyl-octahydro-(3aR,7aS)-thieno[3,2,c]pyridine-(6S)-carboxamide To a high pressure hydrogenation vessel was placed 10.5 g (28.2 mmol) of the subtitled compound of Example 3B and 105 g of 5% palladium-on-carbon in 1100 mL of tetrahydrofuran and 525 mL of ethanol. The resultant reaction mixture was placed under hydrogen (3000 psi) at 80° C. for twenty four hours. The reaction mixture was cooled, filtered to remove the catalyst, and then the catalysts was washed with 20% methanol in chloroform. The resultant organic portions were combined and concentrated under reduced pressure to provide a crude oil. This oil was redissolved in methylene chloride and purified using flash chromatography (SiO$_2$; eluent of 2% methanol in methylene chloride (on a smaller scale, an eluent of 1:2 diethyl ether in hexane containing 2% methanol)) to provide the desired cis isomer (major) comes through with a small amount of a minor isomer. This mixture was recrystallized from a mixture of 1.5 mL methanol/20 mL diethyl ether/120 mL hexane to provide crystals that were filtered, washed with cold hexane and dried under reduced pressure to provide 2.54 g of the cis isomer (24%).

$^1$H NMR (300 MHz, CDCl$_3$ ): δ7.37 (s, 5H); 6.0 and 5.5 (br.s, 1H); 5.18 (br.s, 2H); 4.22 (m, 2H); 3.40 (m, 1H); 2.87 (m, 3H); 2.48 (m, 1H); 2.15 (m, 2H); 1.70 (m, 1H); and 1.15 (br. s, 9H).

MS: m/e 377 (M$^+$ +1).

D. N-t-Butyl-octahydro-(3aR,7aS)-thieno[3,2-c]pyridine-(6S)-carboxamide

To a mixture of 2.41 g (6.4 mmol) of the subtitled compound of Example 3C in 12 mL of a 1:1 acetonitrile/methylene chloride solution, was added 1.9 mL of trimethylsilyliodide. After approximately ten minutes, an additional 0.94 mL of trimethylsilyliodide was added, followed by another 0.48 mL after ten minutes. The resultant mixture was reacted for approximately thirty minutes. When the reaction was substantially complete, as indicated by TLC, (5% ethyl acetate in methylene chloride), the reaction mixture was diluted with 30 mL of diethyl ether, 40 mL of water and 6 mL of a 1N hydrochloric acid solution. The resultant layers were separated and the organic layer was washed with 15 mL of a 0.1N hydrochloric acid solution. The combined aqueous portions were adjusted to pH 8 by the addition of a saturated sodium bicarbonate solution. The desired compound was extracted from the resultant solution using 200 mL of methylene chloride which was then dried with sodium sulfate, filtered and concentrated under reduced pressure to provide 1.3 g of the subtitled compound (84%).

$^1$H NMR (300 MHz, CDCl$_3$): δ6.43 (s, 1H); 3.22 (m, 2H); 2.95 (m, 4H); 2.17 (m, 3H); 2.0 (m, 1H); 1.55 (m, 2H); and 1.32 (s, 9H).

[α$_D$]$_{589}$ (EtOH)=−179.1° (at 22° C.).

EXAMPLE 4

(±)-N-t-Butyl-octahydro-(3aR*,7aS*)-thieno[3,2-c]pyridine-(6S*)-carboxamide

The titled compound was prepared substantially in accordance with the procedure detailed in Example 3A–D, using the titled compound from Example 2.

EXAMPLE 5

N-t-Butyl-octahydro-5[2R-hydroxy-4-phenyl-3S-N(benzyloxycarbonyl)amino-butyl]-(3aR,7aS)-thieno[3,2-c]pyridine-(6S)-carboxamide A solution containing 145 mg (0.487 mmol) of 1S-[(1'S-N-(benzyloxycarbonyl)amino-2'-phenylethyl]oxirane and 118 mg (0.487 mmol) of the subtitled compound from Example 4 in 3 mL of ethanol was heated to 65° C. and reacted for approximately twenty hours. The resultant mixture was concentrated under reduced pressure to provide a crude material. This material was purified using radial chromatography (2000 micron plate; eluent of 1% methanol in chloroform) which separated the diastereomers to provide 98 mg of the titled compound (36%).

$^1$H NMR (300 MHz, CDCl$_3$): δ7.25 (m, 10H); 6.05 (m, 1H); 5.13 (m, 1H); 5.02 (s, 2H); 3.97 (m, 1H); 3.80 (m, 1H); 3.37 (m, 1H); 3.22 (m, 2H); 2.95 (m, 4H); 2.70 (m, 2H); 2.58 (m, 1H); 2.43 (m, 1H); 2.32 (m, 1H); 2.10 (m, 3H); 1.90 (m, 1H); and 1.30 (s, 9H).

MS: m/e 540 (M$^+$).

In addition, 109 mg of another diasteromer was isolated from the reaction mixture (41%).

EXAMPLE 6

N-t-Butyl-octahydro-5[2R-hydroxy-4-phenyl-3S-amino-butyl]-(3aR,7aS)-thieno[3,2-c]pyridine-(6S)-carboxamide The desired subtitled compound was prepared substantially in accordance with the procedure detailed in Example 3D, using 85 mg (0.158 mmol) of the titled compound of Example 5, 101 μL (71 mmol) of trimethylsilyliodide in a 1:1 acetonitrile/methylene chloride mixture to provide 64 mg of a white solid (quantitative).

$^1$H NMR (300 MHz, CDCl$_3$): δ7.28 (m, 5H); 6.38 (s, 1H); 3.75 (m, 1H); 3.32 (m, 2H); 3.12 (m, 1H); 2.93 (m, 2H); 2.78 (m, 2H); 2.58 (m, 3H); 2.38 (m, 1H); 2.12 (m, 5H); 1.83 (m, 2H); and 1.35 (s, 9H).

EXAMPLE 7

N-t-Butyl-octahydro-5[2R-hydroxy-4-thiophenyl-3R-N(benzyloxycarbonyl)amino-butyl]-(3aR,7aS)-thieno[3,2-c]pyridine-(6S)-carboxamide A solution containing 1.45 g (4.4 mmol) of 1S-[(1'R-N-(benzyloxycarbonyl)amino-2'-(phenylthio)ethyl]oxirane and 1.07 g (4.4 mmol) of the subtitled compound from Example 3D in 30 mL of ethanol was heated to 65° C. and reacted for approximately sixty hours. The resultant mixture was concentrated under reduced pressure to provide a foam. This foam was purified using radial chromatography (4000 micron plate; eluent of 1% methanol in methylene chloride) to provide 1.8 g of the desired titled compound. Mixed fractions were combined to provide 326 mg of mixed diastereomers which were again purified using radial chromatography (2000 micron plate; eluent of 1% methanol in methylene chloride to provide an additional 228 mg of the desired compound.

Total yield: 2.03 g (80.5%).

$^1$H NMR (300 MHz, CDCl$_3$): δ7.30 (m, 10H); 5.80 (m, 2H); 5.08 (AB, 2H); 3.95 (m, 2H); 3.42 (m, 2H); 3.17 (m, 3H); 2.90 (m, 2H); 2.67 (m, 1H); 2.58 (m, 1H); 2.48 (m, 1H); 2.35 (m, 2H); 1.98 (m, 4H); and 1.30 (s, 9H).

EXAMPLE 8

N-t-Butyl-octahydro-5[2R-hydroxy-4-thiophenyl-3R-amino-butyl]-(3aR,7aS)-thieno[3,2-c]pyridine-(6S)-carboxamide The desired titled compound was prepared substantially in accordance with the procedure detailed in Example 3D, using 1.8 g (3.15 mmol) of the subtitled compound of Example 7, 2.1 mL of trimethylsilyliodide in 20 mL of a 1:1 acetonitrile/methylene chloride mixture to provide 1.18 g of a white solid (86%).

$^1$H NMR (300 MHz, CDCl$_3$): δ7.38 (m, 2H); 7.28 (m, 2H); 7.20 (m, 1H); 6.23 (s, 2H); 3.65 (s, 1H); 3.28 (m, 3H); 2.90 (m, 4H); 2.70 (m, 2H); 2.58 (m, 1H); 2.43 (m, 1H); 2.34 (m, 1H); 2.05 (m, 4H); 1.80 (m, 3H); and 1.32 (s, 9H).

IR (CHCl$_3$): 3430; 3005; 2973; 1670; 1514; 1456; 1366; and 1090 cm$^{-1}$.

MS: m/e 437 (M$^+$).

EXAMPLE 9

A. (±)-cis-2-Isopropyl-3-tetrahydrothiomhene succinimidyl carbonate

To a solution of 1.75 g (11.97 mmol) of (±)-cis-2-isopropyl-3-hydroxy-tetrahydrothiophene in 12 mL of acetonitrile, was added 5.0 mL of triethylamine followed by 4.61 g (18.0 mmol) of N,N'-disuccinimidyl carbonate. The resultant reaction mixture was allowed to react at room temperature for approximately six hours and then was concentrated under reduced pressure to provide a residue. This residue was redissolved in ethyl acetate and the desired compound was isolated using column chromatography (60 g SiO$_2$; eluent of 40% ethyl acetate in hexane. The fractions containing the desired compound were combined and concentrated under reduced pressure to provide an oil. This oil was redissolved in ethyl acetate and the resultant solution was washed with a saturated sodium bicarbonate solution, dried over sodium sulfate, filtered and then concentrated under reduced pressure to provide 1.75 g of a yellow oil (51%).

$^1$H NMR (300 MHz, CDCl$_3$): δ5.42 (m, 1H); 3.24 (m, 1H); 3.02 (m, 2H); 2.84 (s, 4H); 2.52 (m, 1H); 2.02 (m, 2H); and 1.0 (m, 6H).

B. N-t-Butyl-octahydro-5[2R-hydroxy-3R-N(2'R-isopropyl-tetrahydrothiophen-3'R-yloxycarbonyl)amino-4-phenylthio-)-butyl]-(3aR,7aS)-thieno[3,2-c]pyridine-(6S)-carboxamide and
N-t-Butyl-octahydro-5[2R-hydroxy-3R-N(2'S-isopropyl-tetrahydrothiophen-3'S-yloxycarbonyl)amino-4-phenylthio)-butyl]-(3aR,7aS)-thieno[3,2-c]pyridine-(6S)-carboxamide To 40 mg (0.0915 mmol) of the titled compound from Example 8 in 1 mL of methylene chloride, was added 26 µL (0.184 mmol) of triethylamine followed by 27 mg (0.092 mmol) of the subtitled compound from Example 9A. The resultant reaction mixture was allowed to react for approximately thirty minutes at room temperature and then reduced to dryness under reduced pressure to provide a residue. This residue was redissolved in methylene chloride and purified using chromatography (eluent of 50% ethyl acetate in hexane) to provide the subtitled compounds.

Yield: 24 mg.

$^1$H NMR (300 MHz, CDCl$_3$): δ7.30 (m, 5H); 5.88 (s, 1H); 5.44 (d, J=8 Hz, 1H); 5.37 (s, 1H); 3.88 (m, 2H); 3.35 (m, 2H); 3.18 (m, 3H); 2.90 (m, 4H); 2.65 (m, 2H); 2.55 (m, 1H); 2.35 (m, 3H); 1.95 (m, 5H); 1.35 (s, 9H); and 0.95 (m, 6H).

Yield: 23 mg $^1$H NMR (300 MHz, CDCl$_3$H): δ7.30 (m, 5H); 5.84 (s, 1H); 5.60 (d, J=8 Hz, 1H); 5.37 (m, 1H); 3.94 (m, 1H); 3.86 (m, 1H); 3.35 (m, 2H); 3.20 (m, 3H); 2.90 (m, 4H); 2.65 (m, 2H); 2.53 (m, 1H); 2.35 (m, 3H); 1.98 (m, 5H); 1.35 (s, 9H); and 0.98 (m, 6H).

EXAMPLE 10

A. (±)-cis-1,1-dioxo-2-isopropyl-3-tetrahydrothiphene succinimidyl carbonate

To a cold (0° C.) solution of 1.63 g (5.68 mmol) of the subtitled compound from Example 9A in 50 mL of methylene chloride, was added 2.36 g (11.64 mmol) of 85% m-chloroperoxybenzoic acid (MCPBA). The resultant reaction mixture was warmed to room temperature, reacted for approximately two hours and then diluted with 30 mL of methylene chloride. The resultant mixture was combined with 50 mL of a saturated sodium bicarbonate solution and the resultant layers were separated. The organic layer was dried over sodium sulfate, filtered and concentrated under reduced pressure to provide 1.63 g of a white foam (90%) which was used without further purification.

$^1$H NMR (300 MHz, CDCl$_3$): δ5.52 (m, 1H); 3.24 (m, 2H); 2.82 (s, 4H); 2.78 (m, 1H); 2.60 (m, 1H); 2.35 (m, 1H); 2.18 (m, 1H); 1.22 (d, J=6 Hz, 3H); and 1.02 (d, J=6 Hz, 3H).

B. N-t-Butyl-octahydro-5[2R-hydroxy-3R-N(1',1'-dioxo-2'R-isopropyl-tetrahydrothiophen-3'R-yloxycarbonyl) amino-4-phenylthio-)-butyl]-(3aR,7aS)-thieno[3,2-c] pyridine-(6S)-carboxamide and
N-t-Butyl-octahydro-5[2R-hydroxy-3R-N(1',1'-dioxo-2'S-isopropyl-tetrahydrothiophen-3'S-yloxycarbonyl)amino-4-phenylthio-)-butyl]-(3aR,7aS)-thieno[3,2-c]pyridine-(6S)-carboxamide The subtitled compound was prepared substantially in accordance with the procedure detailed in Example 9B, using 102 mg (0.233 mmol) of the titled compound from Example 8, 67 µL (0.48 mmol) of triethylamine and 77 mg (0.24 mmol) of the subtitled compound from Example 10A in 2 mL of methylene chloride to provide the subtitled compounds.

Yield: 52 mg.

$^1$H NMR (300 MHz, CDCl$_3$): δ7.30 (m, 5H); 5.82 (s, 1H); 5.67 (d, J=8 Hz, 1H); 5.48 (m, 1H); 3.88 (m, 2H); 3.35 (m, 2H); 3.18 (m, 3H); 2.90 (m, 2H); 2.65 (m, 3H); 2.55 (m, 1H); 2.40 (m, 1H); 2.10 (m, 8H); 1.37 (s, 9H); 1.20 (d, J=6 Hz, 3H); and 0.95 (d, J=6 Hz, 3H).

Yield: 51 mg $^1$H NMR (300 MHz, CDCl$_3$): δ7.30 (m, 5H); 5.85 (d, J=8 Hz, 1H); 5.78 (s, 1H); 5.50 (m, 1H); 3.94 (m, 1H); 3.86 (m, 1H); 3.35 (m, 2H); 3.20 (m, 3H); 2.90 (m, 2H); 2.67 (m, 3H); 2.55 (m, 1H); 2.40 (m, 1H); 2.25 (m, 3H); 2.0 (m, 5H); 1.36 (s, 9H); 1.22 (d, J=6 Hz, 3H); and 1.0 (d, J=6 Hz, 3H).

EXAMPLE 11

A. (±)-3-Tetrahydrothiophene succinimidyl carbonate

To a solution of 0.91 g (8.58 mmol) of (±)-hydroxy-tetrahydrothiophene in 10 mL of anhydrous acetonitrile, was added 3.6 mL of triethylamine followed by 3.3 g (12.9 mmol) of N,N'-disuccinimidyl carbonate. The resultant reaction mixture was allowed to react at 23° C. for approximately eighteen hours and then was concentrated under reduced pressure to provide a residue. This residue was redissolved in a mixture of ethyl acetate and saturated solution of sodium bicarbonate. The resultant layers were separated and the organic layer was washed with a saturated brine solution, dried over sodium sulfate, filtered and then concentrated under reduced pressure to provide an oil which was used without further purification.

MS(FD): 245.

B. (±)-3-(1,1-Dioxo-tetrahydrothiophene succinimidyl carbonate

The desired subtitled compound was prepared substantially in accordance with the procedure detailed in Example 10A, using 0.88 g (3.59 mmol) of the subtitled compound from Example 11A and 2.4 g (7.54 mmol) of 55% MCPBA in 5 mL of methylene chloride to provide 1.2 mL of an oil. This oil was purified using flash chromatography (eluent of ethyl acetate) to provide 0.28 g of a sticky white solid (28%).

MS(FD): 278 (100).

C. N-t-Butyl-octahydro-5[2R-hydroxy-3R-N(1',1'-dioxo-tetrahydrothiophen-3'R-yloxycarbonyl)amino-4-phenylthio)-butyl]-(3aR,7aS)-thieno[3,2-c]pyridine-(6S)-carboxamide and N-t-Butyl-octahydro-5[2R-hydroxy-3R-N(1',1'-dioxo-tetrahydrothiophen-3'S-yloxycarbonyl)amino-4-phenylthio)-butyl-]-(3aR,7aS)-thieno[3,2-c]pyridine-(6S)-carboxamide A mixture of 17 mg (0.0622 mmol) of the subtitled compound of Example 11B in 1 mL of methylene chloride was added to a solution of 30 mg (0.068 mmol) of the titled compound from Example 8 and 17 mL of triethylamine in 1 mL of methylene chloride. The resultant reaction mixture was allowed to react for approximately three hours and then was concentrated under reduced pressure to provide a residue. This residue was purified using flash chromatography (eluent of 3.5% methanol in methylene chloride) to provide the subtitled compounds.

Yield: 11 mg (27%).

$^1$H NMR (300 MHz, CDCl$_3$): δ7.20–7.43 (m, 5H); 6.17 (d, J=8 Hz, 1H); 5.78 (br.s, 1H); 5.39 (m, 1H); 4.05 (m, 1H); 3.92 (m, 1H); 1.82–3.43 (m, 22H); and 1.38 (s, 9H).

MS(FD): 600 (100).

Yield: 6 mg (15%).

$^1$H NMR (300 MHz, CDCl$_3$): δ7.18–7.42 (m, 5H); 6.14 (d, J=8 Hz, 1H); 5.80 (br.s, 1H); 5.40 (br.s, 1H); 3.90–4.08 (m, 2H); 3.30–3.42 (m, 3H); 3.03–3.28 (m, 5H); 2.83–3.00 (m, 3H); 2.22–2.70 (m, 7H); 1.80–2.20 (m, 4H); and 1.38 (s, 9H).

MS(FAB) for C$_{27}$H$_{42}$N$_3$O$_6$S$_3$: Calcd: 600.2236; Found: 600.2234.

EXAMPLE 12

N-t-Butyl-octahydro-5[2R-hydroxy-3R-N(1',1'-dioxo-tetrahydrothiophen-3'R-ylmethylcarbonyl)amino-4-phenylthio-butyl]-(3aR,7aS)-thieno[3,2-c]pyridine-(6S)-carboxamide and N-t-Butyl-octahydro-5[2R-hydroxy-3R-N(1',1'-dioxo-tetrahydrothiophen-3'S-ylmethylcarbonyl)amino-4-phenylthio-butyl]-(3aR,7aS)-thieno[3,2-c]pyridine-(6S)-carboxamide To a cold (0° C.) solution containing 46 mg (0.105 mmol) of the titled compound from Example 8, 19 mg (0.105 mmol) of a (±)-3-sulfolanyl acetic acid and 14 mg (0.105 mmol) of hydroxybenzotriazole hydrate (HOBT·H$_2$O) in 1.5 mL of tetrahydrofuran, was added 22 mg (0.105 mmol) of dicyclohexylcarbodiimide (DCC). The reaction mixture was warmed to room temperature and allowed to react for approximately thirty hours. When the reaction was substantially complete, as indicated by TLC, the reaction mixture was diluted with 2 mL of diethyl ether and then filtered through a small cotton plug. The resultant filtrate was concentrated under reduced pressure and then purified using flash chromatography (gradient eluent of 3–4% methanol in methylene chloride) to provide 50 mg of a white foam (79%) which comprised a mixture of the titled compounds.

$^1$H NMR (300 MHz, CDCl$_3$): δ7.18–7.50 (m, 6H); 5.76 (br.s, 1H); 4.33 (m, 1H); 4.10 (m, 1H); 1.80–3.50 (m, 25H); and 1.36 (s, 9H).

MS(FD): 598, 497 (100).

Analysis for C$_{28}$H$_{43}$N$_3$O$_5$S$_3$: Calcd: C, 56.25; H, 7.25; N, 7.03; Found: C, 55.98; H, 7.19; N, 6.90.

EXAMPLE 13

A. (±)-Cis-2-Methyl-3-tetrahydrofuran succinimidyl carbonate

The desired compounds was prepared substantially in accordance with the procedure detailed in Example 9A, using 1.6 g (15.7 mmol) of a racemic mixture of 2(R,S)-methyl-3-hydroxy-furan, 6.7 mL (48 mmol) of triethylamine, and 6.4 g (25 mmol) of N,N'-disuccinimidyl carbonate in 16 mL of acetonitrile to provide a residue. This residue was purified using column chromatography (SiO$_2$; gradient eluent of 10–20% ethyl acetate in methylene chloride) to provide the subtitled compounds.

Yield: 110 mg.

$^1$H NMR (300 MHz, CDCl$_3$): δ5.22 (m, 1H); 4.10 (m, 1H); 3.95 (m, 1H); 3.80 (m, 1H); 2.82 (s, 4H); 2.38 (m, 1H); 2.20 (m, 1H); and 1.35 (d, J=7 Hz, 3H).

NOTE: 90 mg of the trans isomer was also isolated. This compound's peak at chemical shift at ca. δ5.2 is consistent with the cis designation. The analogous compounds' trans isomer had the corresponding chemical shift at δ4.9.

B. N-t-Butyl-octhydro-5 [2R-hydroxy-3R-N(2'R-methyl-tetrahydrofuran-3'R-yloxycarbonyl)amino-4-phenylthio-)-butyl]-(3aR,7aS)-thieno[3,2-c]pyridine-(6S)-carboxamide and N-t-Butyl-octahydro-5[2R-hydroxy-3R-N(2'S-methyl-tetratydrofuran-3'S-yloxycarbonyl)amino-4-phenylthio-)-butyl]-(3aR,7aS)-thieno[3,2-c]pridine-(6S)-carboxamide To a mixture of 36 mg (0.15 mmol) of the subtitled compound from Example 13A (the 110 mg yield isomer) in methylene chloride, was added 58 mg (0.13 mmol) of the titled compound of Example 8, followed by 42 μL of triethylamine. The resultant reaction mixture was allowed to react for approximately two hours. When the reaction was substantially complete, as indicated by thin layer chromatography, the mixture was concentrated under reduced pressure to provide a residue. This residue was redissolved in methylene chloride and then purified using radial chromatography (eluent of 30% ethyl acetate in hexane) to provide the subtitled compounds.

Yield: 17 mg $^1$H NMR (300 MHz, CDCl$_3$): δ7.40 (m, 2H); 7.30 (m, 2H); 7.20 (m, 1H); 5.80 (s, 1H); 5.60 (br.m, 1H); 5.15 (m, 1H); 3.95 (m, 4H); 3.75 (m, 1H); 3.40 (m, 2H); 3.20 (m, 2H); 3.12 (br.s, 1H); 2.90 (m, 2H); 2.65 (m, 2H); 2.50 (m, 1H); 2.30 (m, 3H); 2.00 (m, 5H); 1.36 (s, 9H); and 1.20 (m, 3H).

Yield: 26 mg $^1$H NMR (300 MHz, CDCl$_3$): δ7.40 (m, 2H); 7.30 (m, 2H); 7.20 (m, 1H); 5.80 (s, 1H); 5.75 (br.m, 1H); 5.15 (m, 1H); 3.90 (m, 4H); 3.75 (m, 1H); 3.40 (m, 2H); 3.20 (m, 2H); 3.08 (br. s, 1H); 2.90 (m, 2H); 2.65 (m, 2H); 2.60 (m, 1H); 2.50 (m, 1H); 2.30 (m, 3H); 2.00 (m, 5H); 1.35 (s, 9H); and 1.25 (m, 3H).

EXAMPLE 14

A. Quinaldic acid pentafluorophenyl ester

To a mixture of 15.0 g (86.6 mmol) of quinaldic acid and 20.8 g (113 mmol) of pentafluorophenol in 200 mL of tetrahydrofuran, was added 18.3 g (95.3 mmol) ethylene dichloride in one portion. The reaction mixture was stirred vigorously at room temperature for approximately two hours, resulting in the formation of a gummy precipitate. The solution was decanted from the gum, and the gum was washed with methylene chloride. The combined organic layers were diluted with hexane, washed sequentially with 50 mL 0.1N sodiumhydrogensulfate, 50 mL 1N potassium carbonate, and 50 mL brine, dried over sodium sulfate, filtered, and then concentrated under reduced pressure, to provide a pale pink solid. This solid was dissolved in 30 mL of hot diethyl ether, followed by 400 mL of hot hexane. The resultant solution was allowed to cool to room temperature, and then to 0° C. over a period of approximately ninety minutes to provide 21.6 g of colorless needles (73%).

$^1$H NMR (300 MHz, CDCl$_3$): δ7.73 (t, J=7.5 Hz, 1H); 7.86 (t, J=7.9 Hz, 1H); 7.95 (d, J=8.2 Hz, 1H); 8.29–8.42 (m, 3H).

IR (CHCl$_3$): 3035, 2997, 1763, 1522, 1285, 1068, 998, 842 cm$^{-1}$.

Analysis for C$_{16}$H$_6$NO$_2$F$_5$: Calcd: C, 56.65; H, 1.78; N, 4.13; Found: C, 56.66; H, 1.77; N, 4.12.

B. 2S-N(Quinolin-2-ylcarbonyl)amino-3-oxo-3-aminopropanoic acid

A mixture of 17.9 g (51.2 mmol) of the subtitled compound from Example 14A, 6.99 g (46.6 mmol) of L-asparagine monohydrate, 15.7 g (186 mmol) of sodium bicarbonate in 265 mL water and 219 mL dioxane was stirred vigorously overnight at room temperature. The reaction mixture was concentrated under reduced pressure to remove the dioxane, and the resulting aqaeous layer was acidified to pH 3 with 2N sodiumhydrogensulfate. The aqueous layer was then extracted three times with 60 mL 3:1 chloroform/isopropanol mixture. The combined organic layers were washed with 50 mL of a saturated brine solution, dried over sodium sulfate, filtered and then concentrated under reduced pressure to provide a colorless solid. This solid was washed with 500 mL of diethyl ether and 250 mL of hot hexanes to remove residual pentafluorophenol and then dried at 80° C. in a vacuum oven for three hours to provide 10.61 g (79%) of the desired product.

[α]$_D$ +16.54° (DMSO).

$^1$H NMR (300 MHz, DMSO-D$_6$): δ2.68 (dd, J=16.0,4.9 Hz, 1H), 2.81 (dd, J=16.0,5.7 Hz, 1H), 4.74–4.81 (m, 1H), 6.96 (s, 1H), 7.70 (t, J=7.5 Hz, 1H), 7.85 (t, J=7.5 Hz, 1H), 8.05–8.15 (m, 3H), 8.56 (d, J=8.5 Hz, 1H), 9.12 (d, J=8.6 Hz, 1H), 12.8 (s, 1H).

IR (KBr): 3385, 3367, 3216, 1171, 1662, 1523, 1499, 1427, 780, 592 cm$^{-1}$.

MS(FD): m/e 288(M$^+$), 288(100).

Analysis for C$_{14}$H$_{13}$N$_3$O$_4$: Calcd: C, 58.53; H, 4.56; N, 14.63; Found: C, 58.80; H, 4.57; N, 14.56.

C. N-t-Butyl-octahydro-5[2R-hydroxy-3R-phenylthiomethyl-4-aza-5-oxo-6S-(2-oxo-2-amino)ethyl-6-aza-7-oxo-7-quinolin-2-yl)-heptyl]-(3aR,7aS)-thieno[3,2-c]pyridine-(6S)-carboxmide To a solution of 50 mg (0.114 mmol) of the titled compound from Example 8, 35 mg (0.123 mmol) of the subtitled compound from Example 14B and 17 mg (0.123 mmol) of HOBT·H$_2$O in 2 mL of tetrahydrofuran containing 0.2 mL of dimethylformamide, was added 24 mg (0.120 mmol) of DCC. The resultant reaction mixture was allowed to react for approximately sixteen hours at room temperature, then was filtered and concentrated under reduced pressure to provide a tan foam. This foam was purified using radial chromatography (1000 micron plate; eluent of 5% methanol in methylene chloride) to provide 62 mg of the desired compound (75%).

EXAMPLE 15

A. 2-N(Acetyl)amino-4-methylsulfonyl-butanoic acid

A solution of oxone® in 2 mL of water was added to a solution of 300 mg (1.57 mmol) of N-(acetyl)-D-methionine in 2 mL of methanol. The resultant reaction mixture was stirred for approximately sixteen hours and then diluted with 50 mL of methylene chloride and 6 mL of water. The resultant layers were separated and the organic layer was washed with 20% isopropanol in methylene chloride. The combined organic portions were reduced to dryness under reduced pressure to provide 150 mg of a white solid (43%).

B. N-t-Butyl-octahydro-5[2R-hydroxy-3R-phenylthiomethyl-4-aza-5-oxo-6R-N(acetyl)amino-8-methylsulfonyl-octyl]-(3aR,7aS)-thieno[3,2-c]pyridine-(6S)-carboxamide The desired compound was prepared substantially in accordance with the procedure detailed in Example 14B, using 60 mg (0.137 mmol) of the titled compound from Example 8, 33 mg (0.148 mmol) of the subtitled compound from Example 15A and 20 mg (0.148 mmol) of HOBT·H$_2$O and 29 mg (0.142 mmol) of DCC in 2 mL of tetrahydrofuran containing 0.2 mL of dimethylformamide. The crude material was purified using radial chromatography (1000 micron plate; eluent of 8% methanol in ethyl acetate) to provide 59 mg of the desired subtitled compound.

EXAMPLE 16

N-t-Butyl-octahydro-5[2R-hydroxy-3S-phenylmethyl-4-aza-5-oxo-6S-N(t-butoxycarbonyl)amino-7-naphth-2ylsufonyl-heptyl]-(3aR,7aS)-thieno[3,2-c]pyridine-(6S)-carboxamide The desired subtitled compound was prepared substantially in accordance with the procedure detailed in Example 12, using 61 mg (0.15 mmol) of the titled compound from Example 6, 58 mg (0.153 mmol) of 2S-N(ethanoyl)amino-3-naphth-2-ylsulfonyl propanoic acid, 21 mg (0.53 mmol) of HOBT·H$_2$O, and 31 mg (0.15 mmol) of DCC in tetrahydrofuran to provide a residue. This residue was purified using radial chromatography (2000 micron plate; eluent of 4% methanol in methylene chloride) to provide 87 mg of the desired subtitled compound (75%).

$^1$H NMR (300 MHz, CDCl$_3$): δ8.45 (s, 1H); 7.98 (m, 2H); 7.83 (m, 2H); 7.83 (m, 1H); 7.70 (m, 2H); 7.22 (m, 5H); 6.68 (m, 1H); 6.15 (s, 1H); 5.72 (d, J=8 Hz, 1H); 4.45 (m, 1H); 4.20 (m, 1H); 3.95 (m, 1H); 3.72 (m, 1H); 3.45 (m, 1H); 3.25 (m, 3H); 2.93 (m, 4H); 2.70 (m, 2H); 2.55 (m, 1H); 2.38 (m, 2H); 2.07 (m, 2H); 1.90 (m, 2H); 1.40 (s, 9H); and 1.30 (s, 9H).

EXAMPLE 17

A. N-t-Butyl-octahydro-5[2R-hydroxy-3S-phenylmethyl-4-aza-5-oxo-6S-amino-7-naphth-2-ylsulfonyl-heptyl]-(3aR,7aS)-thieno[3,2-c]pyridine-(6S)-carboxamide The desired subtitled compound was prepared substantially in accordance with the procedure detailed in Example 19A, using 85 mg (0.111 mmol) of the subtitled compound of Example 16 and 2 mL of trifluoroacetic acid in 2 mL of methylene chloride to provide 92 mg of a solid that was used without further purification.

B. N-t-Butyl-octahydro-5[2-hydroxy-3S-phenylmethyl-4-aza-5-oxo-6S-N(methylsulfonyl)amino-7-naphth-2-ylsulfonyl-heptyl]-(3aR,7aS)-thieno[3,2-c]pyridine-(6S)-carboxamide The desired subtitled compound was prepared substantially in accordance with the procedure detailed in Example 19B, using 74 mg (0.111 mmol) of the subtitled compound of Example 17A, 18 μL of N-methylmorpholine and 112 μL of a methanesulfonylchloride solution (100 μL of methanesulfonylchloride in 1 mL of methylene chloride) in of methylene chloride to provide a residue. This residue was purified using radial chromatography (1000 micron plate; eluent of 2% methanol in chloroform) to provide 24 mg of the desired subtitled compound.

$^1$H NMR (300 MHz, CDCl$_3$): δ8.55 (s, 1H); 8.07 (m, 2H); 7.98 (d, J=6 Hz, 1H); 7.85 (d, J=6 Hz, 1H); 7.72 (m, 2H); 7.40 (d, J=8 Hz, 1H); 7.15 (m, 5H); 7.00 (m, 1H); 6.08 (s, 1H); 5.98 (m, 1H); 4.60 (m, 1H); 4.35 (m, 1H); 3.95 (m, 1H); 3.40 (m, 1H); 3.25 (m, 3H); 3.25 (m, 3H); 2.98 (m, 4H); 2.95 (s, 3H); 2.72 (m, 2H); 2.42 (m, 3H); 2.08 (m, 4H); and 1.35 (s, 9H).

C. N-t-Butyl-octahydro-5[2R-hydroxy-3S-phenylmethyl-4-aza-5-oxo-6S-N(trifluoromethylcarbonyl)amino-7-naphth-2-ylsulfonyl-heptyl]-(3aR,7aS)-thieno[3,2-c]pyridine-(6S)-carboxamide The desired subtitled compound was isolated from the reaction mixture from Example 17B.

$^1$H NMR (300 MHz, CDCl$_3$): δ8.50 (s, 1H); 8.05 (m, 2H); 7.98 (d, J=6 Hz, 1H); 7.82 (d, J=6 Hz, 1H); 7.72 (m, 2H); 7.55 (d, J=8 Hz, 1H); 7.15 (m, 5H); 6.95 (m, 1H); 5.95 (m, 1H); 4.98 (m, 1H); 4.35 (m, 1H); 3.98 (m, 1H); 3.30 (m, 3H); 3.17 (m, 1H); 2.95 (m, 4H); 2.70 (m, 2H); 2.45 (m, 3H); 2.05 (m, 4H); and 1.33 (s, 9H).

EXAMPLE 18

N-t-Butyl-octahydro-5[2R-hydroxy-3S-phenylmethyl-4-aza-5-oxo-6S-N(t-butoxycarbonyl)amino-7-p-fluorophenylsulfonyl-heptyl]-(3aR,7aS)-thieno[3,2-c]pyridine-(6S)-carboxamide The titled compound was prepared substantially in accordance with the procedure detailed in Example 16, using 6 mg (0.15 mmol) of the titled compound of Example 6, 0.53 g (0.15 mmol) of 2S-N(t-butoxycarbonyl)amino-3-p-fluorophenylsulfonyl propanoic acid, 21 mg (0.15 mmol) of HOBT·H$_2$O, and 31 mg (0.15 mmol) of DCC in 2 mL of tetrahydrofuran to provide a crude material. This material was purified using radial chromatography (2000 micron plate; gradient eluent of 3–4% methanol in methylene chloride) to provide 90 mg of the desired compound (82%).

$^1$H NMR (300 MHz, CDCl$_3$): δ7.90 (m, 2H); 6.77 (m, 1H); 6.08 (s, 1H); 5.68 (d, J=8 Hz, 1H); 4.42 (m, 1H); 4.20 (m, 1H); 3.92 (m, 1H); 3.45 (m, 2H); 3.25 (m, 3H); 2.93 (m, 4H); 2.70 (m, 2H); 2.55 (m, 1H); 2.38 (m, 2H); 2.08 (m, 2H); 1.93 (m, 2H); 1.44 (s, 9H); and 1.35 (s, 9H).

EXAMPLE 19

A. N-t-Butyl-octahydro-5[2R-hydroxy-3S-phenylmethyl-4-aza-5-oxo-6S-amino-7-p-fluorophenylsulfonyl-heptyl]-(3aR,7aS)-thieno[3,2-c]pyridine-(6S)-carboxamide To a solution of 90 mg (0.123 mmol) of the titled compound of Example 18 in 2 mL of methylene chloride, was added 2 mL of trifluoroacetic acid. After approximately thirty minutes, the reaction mixture was diluted with 15 mL of methylene chloride, washed with a saturated sodium bicarbonate solution, dried over sodium sulfate, filtered and then concentrated under reduced pressure to provide an oil which crystallized on standing. The crystals were redissolved in a methylene chloride/diethyl ether mixture, followed by the addition of hexane. The resultant mixture was reduced to dryness under reduced pressure to provide a white solid which was used without further purification.

B. N-t-Butyl-octahydro-5[2R-hydroxy-3S-phenylmethyl-4-aza-5-oxo-6S-N(methylsulfonyl)amino-7-p-fluorophenylsulfonyl-heptyl]-(3aR,7aS)-thieno[3,2-c]pyridine-(6S)-carboxamide To a cold (0° C.) solution of 78 mg (0.123 mmol) of the subtitled compound from Example 19A and 21 μL (0.123 mmol) of N-methylmorpholine in 2 mL of methylene chloride, was added 126 μL (0.11 mmol) of a methanesulfonylchloride solution (100 μL methanesulfonylchloride in 1 mL of methylene chloride). After approximately ten minutes, the reaction mixture was concentrated under reduced pressure to provide a volume of 0.1 mL which was tested with TLC for the presence of starting material. The reaction mixture was purified using radial chromatography (1000 micron plate; eluent of 2% methanol in chloroform) to provide 20 mg of the desired subtitled compound.

$^1$H NMR (300 MHz, CDCl$_3$): δ7.95 (m, 2H); 7.42 (d, J=8 Hz, 1H); 7.20 (m, 8H); 6.05 (m, 1H); 5.95 (s, 1H); 4.50 (m, 1H); 4.35 (m, 1H); 3.92 (m, 1H); 3.38 (m, 1H); 3.23 (m, 3H); 2.98 (m, 3H); 2.95 (s, 3H); 2.70 (m, 3H); 2.55 (m, 1H); 2.30 (m, 3H); 2.05 (m, 3H); and 1.35 (s, 9H).

MS: m/e 713(M$^+$).

C. N-t-Butyl-octahydro-5[2R-hydroxy-3S-phenylmethyl-4-aza-5-oxo-6S-N(trifluoromethylcarbonyl)amino-7-p-fluorophenylsulfonyl-heptyl]-(3aR,7aS)-thieno[3,2-c]pyridine-(6S)-carboxamide The subtitled compound was isolated from the reaction mixture described in Example 19B.

$^1$H NMR (300 MHz, CDCl$_3$): δ7.90 (m, 2H); 7.55 (d, J=8 Hz, 1H); 7.22 (m, 8H); 5.78 (s, 1H); 4.80 (m, 1H); 4.38 (m, 1H); 3.95 (m, 1H); 3.30 (m, 3H); 3.10 (m, 2H); 2.95 (m, 3H); 2.70 (m, 3H); 2.50 (m, 1H); 2.37 (m, 2H); 2.20 (m, 1H); 2.03 (m, 3H); and 1.35 (s, 9H).

MS: m/e 731 (M$^+$).

EXAMPLE 20

A. N-t-Butyl-octahydro-5[2R-hydroxy-3R-phenylthiomethyl-4-aza-5-oxo-6S-N(t-butoxycarbonyl)amino-7-p-fluorophenylsulfonyl-heptyl]-(3aR,7aS)-thieno[3,2-c]pyridine-(6S)-carboxamide The titled compound was prepared substantially in accordance with the procedure detailed in Example 16, using 80 mg (0.183 mmol) of the titled compound of Example 8, 64 mg (0.183 mmol) of 2S-N(t-butoxycarbonyl)amino-3-p-fluoro-phenylsulfonyl propanoic acid, 25 mg (0.183 mmol) of HOBT·H$_2$O, and 38 mg (0.183 mmol) of DCC in 2.5 mL of tetrahydrofuran to provide a crude material. This material was purified using flash chromatography (gradient eluent of 3–4% methanol in methylene chloride) to provide 130 mg of a white foam (93%).

MS(FD): 768, 666 (100).

EXAMPLE 21

A. N-t-Butyl-octahydro-5[2R-hydroxy-3R-phenylthiomethyl-4-aza-5-oxo-6S-amino-7-p-fluorophenylsulfonyl-heptyl]-(3aR,7aS)-thieno[3,2-c]pyridine-(6S)-carboxamide The desired subtitled compound was prepared substantially in accordance with the procedure detailed in Example 19A, using 0.13 g (0.169 mmol) of the titled compound of Example 20 and 1 mL of trifluoroacetic acid in 1 mL of methylene chloride to provide 100 mg of a solid that was used without further purification.

B. N-t-Butyl-octahydro-5[2R-hydroxy-3R-phenylthiemethyl-4-aza-5-oxo-6S-N(acetyl)amino-7-p-fluorophenylsulfonyl-heptyl]-(3aR,7aS)-thieno[3,2-c]pyridine-(6S)-carboxamide The desired subtitled compound was prepared substantially in accordance with the procedure detailed in Example 19B, using 0.10 g (0.150 mmol) of the subtitled compound of Example 21A, 44 µL of triethylamine and 12 µL of acetyl chloride in 1 mL of methylene chloride. The crude material was purified using flash chromatography (SiO$_2$; eluent of 2% methanol in methylene chloride) to provide 44 mg of a white solid (40%).

$^1$H NMR (300 MHz, CDCl$_3$): δ7.92–7.97 (m, 2H); 7.64 (d, J=8 Hz, 1H); 7.30–7.40 (m, 2H); 7.10–7.30 (m, 5H); 6.92 (d, J=7 Hz, 1H); 5.89 (br.s, 1H); 4.97 (m, 1H); 4.05–4.25 (m, 2H); 3.59–3.70 (m, 2H); 3.18–3.30 (m, 4H); 2.80–3.00 (m, 2H); 2.50–2.75 (m, 2H); 2.22–2.50 (m, 3H); 1.96 (m, 3H); 1.78–2.10 (s, 5H); and 1.33 (s, 9H).

MS(FD): 709, 608.

EXAMPLE 22

N-t-Buty-octahydro-5[2R-hydroxy-3S-phenylmethyl-4-aza-5-oxo-6S-N(acetyl)amino-7-p-fluorophenylsulfonyl-heptyl]-(3aR,7aS)-thieno[3,2-c]-pyridine-(6S)-carboxamide The desired subtitled compound was prepared substantially in accordance with the procedure detailed in Example 19B, using 75 mg (0.118 mmol) of the subtitled compound of Example 19A, 21 µL (0.118 mmol) of triethylamine and 8.4 µL (0.118 mmol) of acetyl chloride in 2 mL of methylene chloride to provide 70 mg of a colorless glassy material. This material was purified using radial chromatography (gradient eluent of 2.5–5% methanol in ethyl acetate) to provide 64 mg of a white foam. This foam was further purified using HPLC (eluent of 30% water in methanol) to provide the desired titled compound (purity>96%).

MS(FD): 676.

EXAMPLE 23

(Alternate Preparation of Example 19C)
N-t-Butyl-octahydro-5[2R-hydroxy-3S-phenylmethyl-4-aza-5-oxo-6S-N(trifluoromethylcarbonyl)amino-7-p-fluorophenylsulfonyl-heptyl]-(3aR,7aS)-thieno[3,2-c]pyridine-(6S)-carboxamide A solution of 73 mg (0.115 mmol) of the subtitled compound of Example 19A and 22 µL (0.172 mmol) of S-ethyl trifluorothioacetate (CF$_3$COSCH$_2$CH$_3$) in 2 mL of ethanol was reacted at room temperature for approximately forty eight hours. When the reaction was substantially complete, as indicated by thin layer chromatography, the resultant mixture was concentrated under reduced pressure to provide 100 mg of a colorless gum and 40 mg of the starting amine (compound of Example 19A). The gum was purified using radial chromatography (gradient eluent of 5–7% methanol in ethyl acetate) to provide 28 mg of the desired titled compound. The recovered amine was reacted substantially as described above using 4 drops of S-ethyl trifluorothioacetate to provide an additional 20 mg of the desired titled compound.

Total yield: 48 mg.

EXAMPLE 24

A. N-t-Butyl-octahydro-5[2R-hydroxy-3S-phenylmethyl-4-aza-5-oxo-6S-N(t-butoxycarbonyl)amino-7-quinolin-8-yl-sulfonyl-heptyl]-(3aR,7aS)-thieno[3,2-c]pyridine-(6S)-carboxamide The desired subtitled compound was prepared substantially in accordance with the procedure detailed in Example 12, using 290 mg (0.72 mmol) of the titled compound from Example 6, 274 mg (0.72 mmol) of 2S-N(t-butoxycarbonyl)amino-3-quinolin-8-ylsulfonyl propanoic acid, 98 mg (0.72 mmol) of HOBT·H$_2$O, and 149 mg (0.72 mmol) of DCC in 7 mL of tetrahydrofuran to provide a brownish foam. This foam was purified using radial chromatography (eluent of 2.5% methanol in ethyl acetate) to provide 380 mg of a white glassy material.

Yield: 75%.

Analysis for C$_{39}$H$_{53}$N$_5$O$_7$S$_2$: Calcd: C, 60.99; H, 6.96; N, 9.12; Found: C, 60.75; H, 6.96; N, 8.95.

B. N-t-Butyl-octahydro-5[2R-hydroxy-3S-phenylmethyl-4-aza-5-oxo-6S-N(trifluoromethylcarbonyl)amino-7-quinolin-8-ylsulfonyl-heptyl]-(3aR,7aS)-thieno[3,2-c]pyridine-(6S)-carboxamide First, 76 mg (0.099 mmol) of the subtitled compound of Example 24A and 2 mL of trifluoroacetic acid were reacted substantially in accordance with the procedure detailed in Example 19A in 1 mL of methylene chloride to provide a residue. This residue was combined with 4 drops of S-ethyl trifluorothioacetate in 2 mL of ethanol and the resultant reaction mixture was reacted substantially in accordance with the procedure detailed in Example 23 to provide a crude material. This material was purified using radial chromatography (eluent of 2% methanol in methylene chloride) to provide 46 mg of a white powder.

EXAMPLE 25

N-t-Butyl-octahydro-5[2R-hydroxy-3S-phenylmethyl-4-aza-5-oxo-6S-N(acetyl)amino-7-quinolin-8-ylsulfonyl-heptyl]-(3aR,7aS)-thieno[3,2-c]pyridine-(6S)-carboxamide First, 100 mg (0.13 mmol) of the subtitled compound of Example 24A and 1.5 mL of trifluoroacetic acid were reacted substantially in accordance with the procedure detailed in Example 19A in 1.5 mL of methylene chloride to provide a residue. This residue was then redissolved in 1.5 mL of methylene chloride and combined with 20 µL (0.143 mmol) of triethylamine followed by the addition of 10.2 µL (0.143 mmol) of acetyl chloride. The resultant reaction mixture was reacted substantially in accordance with the procedure detailed in Example 19B to provide 80 mg of a glassy solid. This material was purified using radial chromatography (eluent of 3% methanol in methylene chloride) to provide 52 mg of a white powder.

Analysis for C$_{36}$H$_{47}$N$_5$O$_6$S$_2$: Calcd: C, 60.91; H, 6.67; N, 9.87; Found: C, 60.85; H, 6.37; N, 9.60.

EXAMPLE 26

N-t-Butyl-octahydro-5[2R-hydroxy-3S-phenylmethyl-4-aza-5-oxo-6S-N(methylsulfonyl)amino-7-quinolin-8-ylsulfonyl-heptyl]-(3aR,7aS)-thieno[3,2-c]pyridine-(6S)-carboxamide The desired titled compound was prepared substantially in accordance with the procedure detailed in Example 25, by first reacting 51 mg (0.066 mmol) of the subtitled compound of Example 24A and 1 mL of trifluoroacetic acid in 1 mL of methylene chloride to provide a residue. This residue was then redissolved in 1 mL of methylene chloride and combined with 18.4 µL (0.132 mmol) of triethylamine and 5.6 µL (0.072 mmol) of methanesulfonylchloride to provide a crude material. This material was purified using radial chromatography (eluent of 3% methanol in methylene chloride containing 0.1% ammonium hydroxide) to provide 18 mg of a white powder.

EXAMPLE 27

A. N-t-Butyl-octahydro-5[3-hydroxy-3S-phenylmethyl-4-aza-5-oxo-6S-N(t-butoxycarbonyl)amino-7-naphth-2-ylsulfonyl-heptyl]-(3aR,7aS)-thieno[3,2-c]pyridine-(6S)-carboxamide The desired subtitled compound was prepared substantially in accordance with the procedure detailed in Example 12, using 220 mg (0.72 mmol) of the titled compound from Example 6, 274 mg (0.72 mmol) of 2S-N(t-butoxycarbonyl)amino-3-naphth-2-ylsulfonyl propanoic acid, 98 mg (0.72 mmol) of HOBT·H$_2$O, and 149 mg (0.72 mmol) of DCC in 7 mL of tetrahydrofuran to provide crude material. This material was purified using radial chromatography (eluent of 2.5% methanol in methylene chloride) to provide 390 mg of a foam.

Yield: 70.7%.
MS(FD): 768.
Analysis for C$_{40}$H$_{54}$N$_4$O$_7$S$_2$: Calcd: C, 62.64; H, 7.10; N, 7.30; Found: C, 62.86; H, 7.18; N, 7.36.

B. N-t-Butyl-octahydro-5[2R-hydroxy-3S-phenylmethyl-4-aza-5-oxo-6S-N(trifluoromethylcarbonyl)amino-7-naphth-2-ylsulfonyl-heptyl]-(3aR,7aS)-thieno[3,2-c]pyridine-(6S)-carboxamide The desired subtitled compound was prepared substantially in accordance with the procedure detailed in Example 24B. First, 154 mg (0.2 mmol) of the subtitled compound of Example 27A and 3 mL of trifluoroacetic acid were reacted in 3 mL of methylene chloride to provide a residue. This residue was then dissolved in 2 mL of acetonitrile and 32 µL (0.25 mmol) of S-ethyl trifluorothioacetate was added. The resultant reaction mixture was monitored by TLC. After approximately twelve hours, an additional 3 drops of S-ethyl trifluorothioacetate was added to the reaction mixture. When the reaction was substantially complete, the crude material was isolated and purified using radial chromatography (eluent of 2% methanol in methylene chloride) to provide 96 mg of a white glassy solid.

EXAMPLE 28

N-t-Butyl-octahydro-5[2R-hydroxy-3S-phenylmethyl-4-aza-5-oxo-6S-N(t-butoxycarbonyl)amino-7-naphth-2-ylsulfonyl-heptyl]-(3aR,7aS)-thieno[3,2-c]pyridine-(6S)-carboxamide The desired titled compound was prepared substantially in accordance with the procedure detailed in Example 25. First, 115 mg (0.15 mmol) of the subtitled compound of Example 24A and 1 mL of trifluoroacetic acid were reacted 1 mL of methylene chloride to provide a residue. This residue was then redissolved in 1 mL of methylene chloride and reacted with 11.7 µL (0.165 mmol) of acetyl chloride in the presence of 23 µL (0.165 mmol) of triethylamine to provide an oil. This oil was purified using radial chromatography (silica, eluent of 3% methanol in methylene chloride) to provide 66 mg of a white powder. Analysis for C$_{37}$H$_{48}$N$_4$O$_6$S$_2$: Calcd: C, 62.69; H, 6.82; N, 7.90; Found: C, 62.68; H, 6.91; N, 7.98.

EXAMPLE 29

N-t-Butyl-octahydro-5[2R-hydroxy-3R-phenylthiomethyl-4-aza-5-oxo-6S-N(trifluoromethylcarbonyl)amino-7-p-fluorophenylsulfonyl-heptyl]-(3aR,7aS)-thieno[3,2-c]pyridine-(6S)-carboxamide The desired subtitled compound was prepared substantially in accordance with the procedure detailed in Example 23, using 0.140 mg (0.210 mmol) of the subtitled compound of Example 21A and 70 µL of S-ethyl trifluorothioacetate in 1 mL of methylene chloride to provide crude material. This material was purified using radial chromatography (eluent of 2% methanol in methylene chloride) to provide 65 mg of the subtitled compound.

Yield: 41%.
$^1$H NMR (300 MHz, CDCl$_3$): δ8.20 (d, J=8 Hz, 1H); 7.95 (m, 3H); 7.30 (m, 7H); 5.62 (m, 1H); 4.90 (m, 1H); 4.25 (m, 2H); 3.75 (m, 2H); 3.30 (m, 4H); 2.90 (m, 2H); 2.42 (m, 6H); 2.0 (m, 4H); and 1.35 (s, 9H).

EXAMPLE 30

A. N-t-Butyl-octahydro-5[2R-hydroxy-3R-phenylthiomethyl-4-aza-5-oxo-6S-N(t-butoxycarbonyl)amino-7-naphth-2-ylsulfonyl-heptyl]-(3aR,7aS)-thieno[3,2-c]pyridine-(6S)-carboxamide The desired subtitled compound was prepared substantially in accordance with the procedure detailed in Example 12, using 120 mg (0.275 mmol) of the titled compound from Example 8, 104 mg (0.275 mmol) of 2S-N(t-butoxycarbonyl)amino-3-naphth-2-ylsulfonyl propanoic acid, 37 mg (0.275 mmol) of HOBT·H$_2$O, and 57 mg (0.275 mmol) of DCC in tetrahydrofuran to provide crude material. This material was purified using radial chromatography (eluent of 2% methanol in methylene chloride) to provide 169 mg of the subtitled compound.

Yield: 77%.
$^1$H NMR (300 MHz, CDCl$_3$): δ8.5 (s, 1H); 7.95 (m, 4H); 7.65 (m, 2H); 7.25 (m, 5H); 5.87 (m, 2H); 4.55 (m, 1H); 4.15 (m, 1H); 4.02 (m, 1H); 3.72 (m, 2H); 3.25 (m, 6H); 2.85 (m, 2H); 2.60 (m, 2H); 2.43 (m, 1H); 2.32 (m, 2H); 1.95 (m, 4H); 1.40 (s, 9H); and 1.32 (s, 9H).

B. N-t-Butyl-octahydro-5[2R-hydroxy-3R-phenylthiomethyl-4-aza-5-oxo-6S-N(trifluoromethylcarbonyl)amino-7-naphth-2-ylsulfonyl-heptyl]-(3aR,7aS)-thieno[3,2-c]pyridine-(6S)-carboxamide A mixture of 154 mg (0.2 mmol) of the subtitled compound of Example 27A and 3 mL of trifluoroacetic acid was reacted in 3 mL of methylene chloride for approximately thirty minutes and then concentrated under reduced pressure to provide a crude material as the trifluoroacetic acid salt. The crude material was then redissolved in 1 mL of methylene chloride and combined with 17.9 mL (0.16 mmol) of N-methylmorpholine, followed by the addition of 12.6 µL (0.16 mmol) of methanesulfonylchloride (stock solution of 100 µL of methanesulfonylchloride in 1 mL of methylene chloride). When the reaction was substantially complete, the desired material was isolated and purified using radial chromatography (eluent of 2% methanol in methylene chloride) to provide 116 mg of the subtitled compound.

Yield: 90%.
$^1$H NMR (300 MHz, CDCl$_3$): δ8.50 (s, 1H); 8.15 (m, 1H); 7.95 (m, 4H); 7.65 (m, 2H); 7.30 (m, 5H); 5.63 (m, 1H); 4.93

(m, 1H); 4.22 (m, 2H); 3.80 (m, 2H); 3.22 (m, 4H); 2.90 (m, 2H); 2.50 (m, 7H); 1.95 (m, 4H); and 1.35 (s, 9H).
MS(FD): m/e 796 (M$^+$ +1).

EXAMPLE 31

A. (±)cis and (±)trans, 2-Methyl-3-hydroxy-tetrahydrothiophene

To a cold (−78° C.) solution of 1.5 g (12.9 mmol) of 2-methyl-tetrahydrothiophene-3-one in 25 mL of tetrahydrofuran, was added dropwise 16.8 mL of 1M diisobutylaluminum hydride (DIBAL) in toluene. The resultant reaction mixture was stirred for approximately thirty minutes, warmed to 0° C. and then stirred for another thirty minutes. To this mixture was slowly added 50 mL of a 1N hydrochloric acid solution and the resultant reaction mixture was then diluted with diethyl ether. The resulting layers were separated and the organic layer was washed sequentially with aqueous sodium bicarbonate, water, brine, dried over magnesium sulfate and then concentrated under reduced pressure to provide 1.0 g of a colorless oil (67%). This oil was used without further purification.

B. (±)cis and (+)trans, 2-Methyl-3-tetrahydrothiophene p-nitrophenyl carbonate

To a cold (0° C.) solution of 0.70 g (5.93 mmol) of the subtitled compound of Example 31A in 5 mL of anhydrous tetrahydrofuran, under nitrogen, was added 1.79 g (8.90 mmol) of p-nitrophenylchloroformate followed by the addition of approximately 2 mg of 4-dimethylaminopyridine (DMAP) and then 1.0 mL (8.90 mmol) of 2,6-lutidine. The resultant reaction mixture was then diluted with an additional 5 mL of tetrahydrofuran, reacted for approximately ten minutes at 0° C. and then three hours at room temperature. The reaction mixture was filtered (using ethyl acetate to wash) to provide approximately 1 g of a white solid. The resulting filtrate was concentrated under reduced pressure to provide 2.3 g of an orange oil. This oil was purified using radial chromatography (4000 micron plate; eluent of 1% ethyl acetate in methylene chloride) to provide mixed fractions: 1.6 g (2:1 cis, trans) and 90 mg (4:1 cis, trans) which were used in Example 31C without further purification.

C. (±)cis and (±)trans, 1,1-Dioxo-2-methyl-3-tetrahydrothiophene -p-nitrophenyl carbonate The desired subtitled compound was prepared substantially in accordance with the procedure detailed in Example 10A, using 0.75 g (2.65 mmol) of the mixture of compounds isolated in Example 31B and 1.7 g (5.4) of MCPBA in 5 mL of methylene chloride to provide 0.88 g of crude material. This material was purified using flash chromatography (eluent of 1:1 ethyl acetate and cyclohexane) to provide the desired compounds.

Analysis for $C_{12}H_{13}NO_7S$: Calcd: C, 45.71; H, 4.16; N, 4.44; Found: C, 45.50; H, 4.26; N, 4.71.

Yield (trans isomers): 0.21 g (25%).

$^1$H NMR (300 MHz, CDCl$_3$): δ8.24 (d, J=7 Hz, 2H); 7.37 (d, J=7 Hz, 2H); 5.04 (q, J=5 Hz, 1H); 3.35 (m, 2H); 3.20 (m, 1H), 2.59 (m, 1H); 2.41 (m, 1H); 1.45 (d, J=7 Hz, 3H).

Yield (cis isomers): 0.32 g of a white solid (38%).

$^1$H NMR (300 MHz, CDCl$_3$/CD$_3$CN): δ8.15 (d, J=7 Hz, 2H); 7.28 (d, J=7 Hz, 2H); 5.38 (m, 1H); 3.22 (m, 1H); 3.08 (m, 2H); 2.39 (m, 2H); 1.22 (d, J=7 Hz, 3H).

D. N-t-Butyl-octahydro-5[2R-hydroxy-3R-N(1',1'-dioxo-2R-methyl-tetrahydrothiophen-3'R-yloxycarbonyl)amino-4-phenylthio)-butyl]-(3aR,7aS)-thieno[3,2-c]pyridine-(6S)-carboxamide and
N-t-Butyl-octahydro-5[2R-hydroxy-3R-N(1',1'-dioxo-2'S-methyl-tetrahydrothiophen-3'S-yloxycarbonyl)amino-4-phenylthio)-butyl]-(3aR,7aS)-thieno[3,2-c]pyridine-(6S)-carboxamide The subtitled compound was prepared substantially in accordance with the procedure detailed in Example 9B, using 0.10 g (0.23 mmol) of the titled compound from Example 8, 64 μL (0.46 mmol) of triethylamine and 72 mg (0.23 mmol) of the (±)cis-subtitled compounds isolated in Example 31C in 3 mL of methylene chloride to provide the subtitled compounds. The crude material was purified using radial chromatography (1000 micron plate; eluent of 3% methanol in methylene chloride) to provide two fractions.

Analysis for $C_{28}H_{43}N_3O_6S_3$: Calcd: C, 54.79; H, 7.06; N, 6.84; Found: C, 54.75; H, 7.07; N, 6.60.

Fraction A

Yield: 30 mg.

MS (FD): 613.

$^1$H NMR (300 MHz, CDCl$_3$): δ7.40 (d, J=8 Hz, 2H); 7.26 (m, 2H); 7.18 (t, J=7 Hz, 1H); 6.00 (d, J=10 Hz, 1H); 5.88 (br.s, 1H); 5.43 (q, J=5 Hz, 1H); 3.93 (m, 2H); 3.35 (m, 2H); 3.30–3.05 (m, 5H), 2.88 (m, 2H); 2.61 (m, 2H); 2.45 (m, 1H); 2.33 (m, 4H); 2.15–1.80 (m, 5H); 1.32 (s, 9H); 1.26 (d, J=8 Hz, 3H).

Fraction B

Yield: 30 mg.

MS (FD): 613.

$^1$H NMR (300 MHz, CDCl$_3$): δ7.40 (d, J=8 Hz, 2H); 7.26 (m, 2H); 7.18 (t, J=7 Hz, 1H); 6.20 (d, J=10 Hz, 1H); 5.90 (br.s, 1H); 5.42 (q, J=5 Hz, 1H); 4.00–3.84 (m, 2H); 3.40–3.08 (m, 6H), 2.88 (m, 3H); 2.60 (m, 2H); 2.46 (m, 1H); 2.33 (m, 4H); 2.17–1.80 (m, 5H); 1.32 (s, 9H) overlapping 1.30 (d, J=8 Hz, 3H).

EXAMPLE 32

Separation of cis(±) and trans(±), 2-Methyl-3-hydroxy-tetrahydrothiophene

The desired cis and trans compounds were separated from 0.68 g of the cis/trans mixture obtained in Example 31A, using HPLC (steel column, Rainin Dynamax CN, on a Waters 4000). The desired compounds were eluted using an eluent of 5% diethyl ether in pentane (at 40 mL/min.).

Yield: 0.30 g of a colorless oil (cis)

$^1$H NMR (300 MHz, CDCl$_3$): δ4.20 (q, J=3 Hz, 1H); 3.46 (m, 1H); 3.03 (m, 1H);2.90 (m, 1H); 2.17 (m, 1H); 1.93 (m, 1H); 1.88 (s, 1H); 1.32 (d, J=7 Hz, 3H).

Yield: 0.16 g of a colorless oil (trans)

$^1$H NMR (300 MHz, CDCl$_3$): δ3.99 (q, J=4 Hz, 1H); 3.17 (m, 2H); 2.85 (m, 2H); 1.98 (m, 1H); 1.19 (d, J=7 Hz, 3H).

EXAMPLE 33

Resolution of (±)cis, 2-Methyl-3-hydroxy-tetrahydrothiophene

A. (±)cis, 2-Methyl-3-acetate-tetrahydrothiophene

To 0.56 g (4.75 mmol) of the cis, (±)-2-methyl-3-hydroxy-tetrahydrothiophene isolated from Example 32 in 3.8 mL of pyridine, was added 12 mg (0.095 mmol) of DMAP and 3.1 mL (33.2 mmol) of acetic anhydride. The resultant reaction mixture was allowed to react overnight at room temperature. When the reaction was substantially complete, the reaction mixture was diluted with diethyl ether and water. The resultant layers were separated and the organic layer was washed sequentially with water, 1N hydrochloric acid, and brine, dried over magnesium sulfate, filtered and then concentrated under reduced pressure to provide 0.8 g of a light yellow oil. This oil was purified using flash chromatography (eluent of 1:1 diethyl ether in hexane) to provide 0.64 g of a colorless oil.

Yield: 84%.

$^1$H NMR (300 MHz, CDCl$_3$): δ5.39 (m, 1H); 3.62 (m, 1H); 3.05 (m, 1H); 2.91 (m, 1H); 2.23 (m, 1H); 2.10 (m, 1H) overlapping 2.10 (s, 3H); 1.23 (d, J=7 Hz, 3H).

B. cis, 2R-methyl-3R-hydroxy-tetrahydrothiophene

A mixture containing 0.64 g of the subtitled compounds of Example 33A, 0.05 mL of Triton® X-100 (Fluka) and 5 mg of lipase PS-800 from *Pseudomonas fluorescens* (Fluka) was heated to 38° C. and allowed to react for approximately eighteen hours. The reaction mixture was then diluted with diethyl ether and the resultant layers were separated and the aqueous layer was extracted twice with 100 mL of diethyl ether. The combined organic portions were dried over magnesium sulfate, filtered and then concentrated under reduced pressure to provide 0.54 g of a colorless oil. This oil was purified using HPLC (steel column, Rainin Dynamax CN on a Waters 4000, eluent of 30% diethyl ether in pentane, 45 mL/min.) to provide 0.18 g of the desired subtitled compound as a colorless oil.

C. cis, 2S-methyl-3S-acetate-tetrahydrothiophene

The subtitled compound was isolated from the reaction mixture described in Example 33B.

Yield: 0.24 g of a colorless oil.

EXAMPLE 34

N-t-Butyl-octahydro-5[2R-hydroxy-3R-N(1',1'-dioxo-2'R-methyl-tetrahydrothiophen-3'S-yloxycarbonyl)amino-4-phenylthio)-butyl]-(3aR, 7aS)-thieno[3,2-c]pyridine-(6S)-carboxamide and N-t-Butyl-octahydro-5[2R-hydroxy-3R-N(1',1'-dioxo-2S-methyl-tetrahydrothiophen-3'R-yloxycarbonyl)amino-4-phenylthio)-butyl]-(3aR, 7aS)-thieno[3,2-c]pyridine-(6S)-carboxamide The subtitled compound was prepared substantially in accordance with the procedure detailed in Example 9B, using 119 mg (0.271 mmol) of the titled compound from Example 8, 75 μL (0.542 mmol) of triethylamine and 90 mg (0.286 mmol) of the (±)trans subtitled compounds isolated in Example 31C in 3 mL of methylene chloride to provide the subtitled compounds. The crude material was purified using radial chromatography (2000 micron plate; eluent of 2% methanol in methylene chloride) to provide two fractions.

Fraction A

Yield: 64 mg of a white solid.

$^1$H NMR (CDCl$_3$): δ7.38 (d, J=7 Hz, 2H); 7.29 (d, J=7 Hz, 2H); 7.20 (m, 1H); 6.14 (d, J=9 Hz, 1H); 5.80 (br.s, 1H); 4.92 (q, J=5 Hz, 1H); 4.00 (m, 2H); 3.40 (d, J=6 Hz, 2H); 3.30–3.02 (m, 5H); 2.90 (m, 3H); 2.60 (m, 2H); 2.43 (m, 2H); 2.33–1.84 (m, 7H); 1.38 (d, 3H) overlapping 1.38 (s, 9H).

Analysis for C$_{28}$H$_{43}$N$_3$O$_6$S$_3$: Calcd: C, 54.79; H, 7.06; N, 6.85; Found: C, 54.53; H, 6.97; N, 6.56.

Fraction B

Yield: 65 mg of a white solid.

$^1$H NMR (CDCl$_3$): δ7.39 (d, J=7 Hz, 2H); 7.28 (d, J=7 Hz, 2H); 7.20 (m, 1H); 6.19 (d, J=9 Hz, 1H); 5.78 (br.s, 1H); 4.90 (q, J=5 Hz, 1H); 4.05 (m, 1H); 3.95 (m, 1H); 3.41 (m, 2H); 3.30–3.02 (m, 5H); 2.90 (m, 3H); 2.60 (m, 2H); 2.42 (m, 2H); 2.30 (m, 2H); 2.20–1.82 (m, 5H); 1.40 (d, J=7 Hz, 3H); 1.35 (s, 9H).

EXAMPLE 35

A. (±)-cis, 2-Methyl-3-hydroxy-tetrahydrothiophene

To a cold (−78° C.) solution of 1.16 g (10 mmol) of 2-methyl-tetrahydrothiophene-3-one in 5 mL of tetrahydrofuran, was added 10 mL of 1M potassium tri-sec-butylborohydride (K-Selectride) in tetrahydrofuran. The resultant reaction mixture was stirred for approximately one hour, warmed to 0° C. and then stirred for another thirty minutes. To this mixture was slowly added 5 mL of a 2N sodium hydroxide solution, followed by 4 mL of hydrogen peroxide. The resultant reaction mixture was then warmed to room temperature, allowed to react for approximately thirty minutes, poured into diethyl ether and then combined with 50 mL of N/10 sodium thiosulfate. The resulting layers were separated, and the organic layer was washed brine, dried over magnesium sulfate, filtered and then concentrated under reduced pressure to provide 0.84 g of a colorless oil. This oil was used without further purification.

Yield: 67%.

$^1$H NMR (300 MHz, CDCl$_3$): δ4.20 (q, J=3 Hz, 1H); 3.46 (m, 1H); 3.03 (m, 1H); 2.90 (m, 1H); 2.17 (m, 1H); 1.93 (m, 1H); 1.88 (s, 1H); 1.32 (d, J=7 Hz, 3H).

EXAMPLE 36

Resolution of cis(±), 2-Methyl-3-hydroxy-tetrahydrothiophene

A. cis, 2R-Methyl-3R-acetate-tetrahydrothiophene

To a mixture of 0.69 g (5.85 mmol) of the (±)cis, 2-methyl-3-hydroxy-tetrahydrothiophene isolated from Example 32 and 1.6 mL (17.5 mmol) of vinyl acetate in 10 mL of acetone, was added 50 mg of lipase SAM-II from *Pseudomonas fluorescens* (Fluka). The resultant reaction mixture was stirred for approximately four days at room temperature. When the reaction was substantially complete, the reaction mixture was concentrated under reduced pressure and then filtered through a cotton plug. The resultant filtrate was then concentrated under reduced pressure to provide 0.8 g of a light yellow oil. This oil was purified using HPLC (steel column, Rainin Dynamax CN on a Waters 4000, eluent of 30% diethyl ether in pentane, 45 mL/min.) to provide 0.44 g of a colorless oil.

Yield: 94%.

$^1$H NMR (300 MHz, CDCl$_3$): δ5.39 (m, 1H); 3.62 (m, 1H); 3.05 (m, 1H); 2.91 (m, 1H); 2.23 (m, 1H); 2.10 (m, 1H) overlapping 2.10 (s, 3H); 1.23 (d, J=7 Hz, 3H).

B. cis, 2S-methyl-3S-hydroxy-tetrahydrothiophene

The subtitled compound was isolated from the reaction mixture of Example 36A.

Yield: 0.25 g of a colorless oil.

$^1$H NMR (300 MHz, CDCl$_3$): δ4.20 (q, J=3 Hz, 1H); 3.46 (m, 1H); 3.03 (m, 1H); 2.90 (m, 1H); 2.17 (m, 1H); 1.93 (m, 1H); 1.88 (s, 1H); 1.32 (d, J=7 Hz, 3H).

EXAMPLE 37

A. cis, 2S-Methyl-3S-tetrahydrothiophene succinimidyl carbonate

The desired subtitled compound was prepared substantially in accordance with the procedure detailed in Example 9A, using 0.29 g (2.5 mmol) of the subtitled compound of Example 36B, 1.02 mL (7.4 mmol) of triethylamine, and 0.94 g (3.7 mmol) of N,N'-disuccinimidyl carbonate in 5 mL of acetonitrile to provide 0.72 g of a light brown oil (51%).

$^1$H NMR (300 MHz, CDCl$_3$): δ5.23 (q, J=4 Hz, 1H); 3.62 (m, 1H); 3.05 (m, 1H); 2.88 (m, 1H); 2.80 (s, 4H); 2.40 (m, 1H); 2.13 (m, 1H); 1.30 (d, J=7 Hz, 3H).

B. cis-1,1-dioxo-2S-Methyl-3S-tetrahydrothiophene succinimidyl carbonate

The desired subtitled compound was prepared substantially in accordance with the procedure detailed in Example 10A, using 0.64 g (2.5 mmol) of the titled compound from Example 37A, 1.6 g (5.07 mmol) of MCPBA to provide crude material. This crude material was triturated in a 2:1 ethyl acetate/methylene chloride mixture and then filtered to provide 0.32 g of a white solid which was used without further purification.

Yield: 44%.

$^1$H NMR (300 MHz, CDCl$_3$): δ5.47 (q, J=4 Hz, 1H); 3.38–3.20 (m, 3H); 2.82 (s, 4H); 2.62–2.39 (m, 2H); 1.39 (d, J=7 Hz, 3H).

C. N-t-Butyl-octahydro-5[2R-hydroxy-3R-N(1',1'-dioxo-2'S-methyl-tetrahydrothiophen-3'S-yloxycarbonyl)amino-4-phenylthio)-butyl]-(3aR,7aS)-thieno[3,2-c]pyridine-(6S)-carboxamide The desired subtitled compound was prepared substantially in accordance with the procedure detailed in Example 9B, using 0.48 g (1.1 mmol) of the titled compound from Example 8, 0.32 g (1.1 mmol) of the subtitled compound from Example 37B, and 0.32 mL (2.31 mmol) of triethylamine in 4 mL of methylene chloride to provide 0.8 g of a crude white solid. This solid was purified using radial chromatography (4000 micron plate; eluent of 3% methanol in methylene chloride) to provide 0.50 g of a white solid.

Yield: 74%.

MS (FD): 613.

$^1$H NMR (300 MHz, CDCl$_3$): δ7.40 (d, J=8 Hz, 2H); 7.26 (m, 2H); 7.18 (t, J=7 Hz, 1H); 6.20 (d, J=10 Hz, 1H); 5.90 (br.s, 1H); 5.42 (q, J=5 Hz, 1H); 4.00–3.84 (m, 2H); 3.40–3.08 (m, 6H), 2.88 (m, 3H); 2.60 (m, 2H); 2.46 (m, 1H); 2.33 (m, 4H); 2.17–1.80 (m, 5H); 1.32 (s, 9H) overlapping 1.30 (d, J=8 Hz, 3H).

D. N-t-Butyl-octahydro-5[2R-hydroxy-3R-N(1',1'-dioxo-2'S-methyl-tetrahydrothiophen-3'S-yloxycarbonyl)amino-4-phenylthio)-butyl]-(3aR,7aS)-thieno[3,2-c]pyridine-(6S)-carboxamide methanesulfonate To a mixture of 0.50 g (0.81 mmol) of the subtitled compound of Example 37C in 5 mL of methylene chloride, was slowly added 53 mL (0.81 mmol) of methanesulfonic acid. The resultant reaction mixture was concentrated under reduced pressure to provide 0.58 g of a white solid (100%).

Analysis for C$_{29}$H$_{47}$N$_3$O$_9$S$_4$: Calcd: C, 49.06; H, 6.67; N, 5.92; Found: C, 48.84; H, 6.53; N, 5.98.

EXAMPLE 38

A. cis, 2R-Methyl-3R-tetrahydrothiophene succinimidyl carbonate

The desired subtitled compound was prepared substantially in accordance with the procedure detailed in Example 9A, using 0.30 g (2.5 mmol) of the subtitled compound of Example 33B, 1.06 g (7.62 mmol) of triethylamine, and 0.98 g (3.8 mmol) of N,N'-disuccinimidyl carbonate in 5 mL of acetonitrile to provide 0.70 g of a light brown oil (51%) which was used without further purification.

B. cis-1,1-dioxo-2R-Methyl-3R-tetrahydrothiophene succinimidyl carbonate

The desired subtitled compound was prepared substantially in accordance with the procedure detailed in Example 10A, using 0.66 g (2.6 mmol) of the titled compound from Example 38A, 1.64 g (5.22 mmol) of MCPBA to provide crude material. This crude material was redissolved in methylene chloride and then washed with a cold saturated sodium bicarbonate solution, dried over sodium sulfate, filtered and reduced to dryness under reduced pressure to provide 0.66 g of a white solid which was used without further purification.

Yield: 44%.

Analysis for C$_{10}$H$_{13}$NO$_7$S: Calcd: C, 41.24; H, 4.50; N, 4.81; Found: C, 41.94; H, 4.30; N, 4.66.

C. N-t-Butyl-octahydro-5[2R-hydroxy-3R-N(1',1'-dioxo-2'R-methyl-tetrahydrothiophen-3'R-yloxycarbonyl)amino-4-phenylthio)-butyl]-(3aR,7aS)-thieno[3,2-c]pyridine-(6S)-carboxamide (Alternate Preparation of 31D, Fraction A)

The desired subtitled compound was prepared substantially in accordance with the procedure detailed in Example 9B, using 0.44 g (1.0 mmol) of the titled compound from Example 8, 0.32 g (1.1 mmol) of the subtitled compound from Example 38B, and 0.28 mL (2.0 mmol) of triethylamine in 3 mL of methylene chloride to provide 0.8 g of a crude white solid. This solid was purified using flash chromatography (silica, eluent of 3.5% methanol in methylene chloride) to provide 0.39 g of a white solid.

Yield: 64%.

D. N-t-Butyl-octahydro-5[2R-hydroxy-3R-N(1',1'-dioxo-2'R-methyl-tetrahydrothiophen-3'-yloxycarbonyl)amino-4-phenylthio)-butyl]-(3aR,7aS)-thieno[3,2-c]pyridine-(6S)-carboxamide methanesulfonate To 0.39 g (0.81 mmol) of the subtitled compound of Example 38C in 5 mL of methylene chloride, was slowly added 41 μL (1.0 mmol) of methanesulfonic acid. The resultant reaction mixture was concentrated under reduced pressure to provide the desired subtitled compound (100%).

Analysis for C$_{29}$H$_{47}$N$_3$O$_9$S$_4$: Calcd: C, 49.06; H, 6.67; N, 5.92; Found: C, 49.15; H, 6.50; N, 5.68.

EXAMPLE 39

Resolution of (±)cis, 2-Isopropyl-3-hydroxy-tetrahydrothiophene

A. (±)cis, 2-Isopropyl-3-acetate-tetrahydrothiophene

To 7.65 g (52.3 mmol) of the cis, (±)-2-isopropyl-3-hydroxy-tetrahydrothiophene in 50 mL of pyridine, was added 1.25 g of DMAP and 38 mL of acetic anhydride. The resultant reaction mixture was allowed to react for approximately twenty hours at room temperature. When the reaction was substantially complete, the reaction mixture was diluted with 200 mL of diethyl ether and water. The resultant layers were separated and the organic layer was washed sequentially with water, 0.1N hydrochloric acid, and a saturated sodium bicarbonate solution, dried over sodium sulfate, filtered and then concentrated under reduced pressure to provide an orange oil. This oil was purified using flash chromatography (eluent of 4% ethyl acetate in hexane) to provide 7.05 g of a slightly yellow oil.

Yield: 84%.

B. cis, 2R-Isopropyl-3R-hydroxy-tetrahydrothiophene

To a mixture of 3.0 g of the subtitled compounds of Example 39A in 48 mL of a 0.05M phosphate buffer (pH 7), was added 0.24 mL of Triton® X-100 (Fluka) and 0.12 g of lipase (SAM II) from *Pseudomonas fluorescens* (Fluka). The resultant reaction mixture was heated to 37°–39° C. and allowed to react overnight. The reaction mixture was then diluted with 50 mL of diethyl ether, the resultant layers were separated and the aqueous layer was extracted twice with 40 mL of diethyl ether. The combined organic portions were dried over sodium sulfate, filtered and then concentrated under reduced pressure to provide a crude material. This material was purified using column chromatography (silica gel, gradient eluent of 2–10% ethyl acetate in hexane) to provide 1.01 g of the desired subtitled compound.

[α]$_D$=+10.04 (CHCl$_3$ c=0.736).

$^1$H NMR (300 MHz, CDCl$_3$): δ4.35 (m, 1H); 2.95 (m, 3H); 2.20 (m, 2H); 2.15 (d, J=8 Hz, 1H); 1.88 (m, 2H); 1.04 (d, J=8 Hz, 3H); and 0.99 (d, J=8 Hz, 3H).

C. cis, 2S-Isopropyl-3S-acetate-tetrahydrothiophene

The subtitled compound was isolated from the reaction mixture described in Example 39B.

Yield: 1.38 g (46%).

EXAMPLE 40

A. cis, 2R-Isopropyl-3R-tetrahydrothiophene succinimidyl carbonate

The desired subtitled compound was prepared substantially in accordance with the procedure detailed in Example 9A, using 600 mg (4.1 mmol) of the subtitled compound of Example 39B, 1.71 mL (12.3 mmol) of triethylamine, and 1.58 mg (6.15 mmol) of N,N'-disuccinimidyl carbonate in acetonitrile to provide a crude material. This material was purified using column chromatography (50 g SiO$_2$; gradient eluent of 30–50% ethyl acetate in hexane) to provide 1.0 g of the desired subtitled compound (85%).

$^1$H NMR (300 MHz, CDCl$_3$): δ5.42 (m, 1H); 3.24 (m, 1H); 3.02 (m, 2H); 2.84 (s, 4H); 2.52 (m, 1H); 2.02 (m, 2H); and 1.0 (m, 6H).

B. cis, 1,1-Dioxo-2R-isopropyl-3R-tetrahydrothiophene succinimidyl carbonate

The desired subtitled compound was prepared substantially in accordance with the procedure detailed in Example 9A, using 1.0 g (3.48 mmol) of the subtitled compound from Example 40A and 1.83 g (7.1 mmol) of 85% m-chloroperoxybenzoic acid (MCPBA) in 50 mL of methylene chloride to provide 1.1 g (100%) which was used without further purification.

$^1$H NMR (300 MHz, CDCl$_3$): δ5.52 (m, 1H); 3.24 (m, 2H); 2.82 (s, 4H); 2.78 (m, 1H); 2.60 (m, 1H); 2.35 (m, 1H); 2.18 (m, 1H); 1.22 (d, J=6 Hz, 3H); and 1.02 (d, J=6 Hz, 3H).

C. N-t-Butyl-octahydro-5[2R-hydroxy-3R-N(1',1'-dioxo-2'R-isopropyl-tetrahydrothiophen-3'-yloxycarbonyl)amino-4-phenylthio-)-butyl]-(3aR,7aS)-thieno[3,2-c]pyridine-(6S)-carboxamide (Alternate preparation of Example 10B (52 mg fraction)

The subtitled compound was prepared substantially in accordance with the procedure detailed in Example 9B, using 100 mg (0.230 mmol) of the titled compound from Example 8, 66 μL (0.473 mmol) of triethylamine and 77 mg (0.24 mmol) of the subtitled compound from Example 40B in 1.5 mL of methylene chloride to provide crude material. This material was purified using radial chromatography (1000 micron plate; gradient eluent of 70–80% ethyl acetate in hexane) followed by radial chromatography (1000 micron plate; gradient eluent of 75–90% ethyl acetate in hexane containing 5% methanol)

Yield: 81%.

$^1$H NMR (300 MHz, CDCl$_3$): δ7.30 (m, 5H); 5.82 (s, 1H); 5.67 (d, J=8 Hz, 1H); 5.48 (m, 1H); 3.88 (m, 2H); 3.35 (m, 2H); 3.18 (m, 3H); 2.90 (m, 2H); 2.65 (m, 3H); 2.55 (m, 1H); 2.40 (m, 1H); 2.10 (m, 8H); 1.37 (s, 9H); 1.20 (d, J=6 Hz, 3H); and 0.95 (d, J=6 Hz, 3H).

D. N-t-Butyl-octahydro-5[2R-hydroxy-3R-N(1',1'-dioxo-2'R-isopropyl-tetrahydrothiophen-3'R-yloxycarbonyl)amino-4-phenylthio-)-butyl]-(3aR,7aS)-thieno[3,2-c]pyridine-(6S)-carboxamide methanesulfonate To 850 mg (1.33 mmol) of the subtitled compound of Example 40C in 12 mL of a 2:1 mixture of methylene chloride/acetonitrile, was slowly added 85.8 μL (1.33 mmol) of methanesulfonic acid. The resultant reaction mixture was concentrated under reduced pressure to provide a residue. This residue was redissolved in diethyl ether and hexane and concentrated under reduced pressure (three times). The resultant solid was sonicated with hexane and concentrated under reduced pressure to provide 965 mg of the desired subtitled compound (99.5%). The following compounds may be prepared in accordance with the procedures detailed above.

N-t-Butyl-octahydro-5[2R-hydroxy-3R-N(1',1'-dioxo-2'R-isopropyl-tetrahydrothiophen-3'R-yloxycarbonyl)amino-4-phenyl)-butyl]-(3aR,7aS)-thieno[3,2-c]pyridine-(6S)-carboxamide;

N-t-butyl-octahydro-5[2R-hydroxy-3R-N(1',1'-dioxo-2'S-isopropyl-tetrahydrothiophen-3'S-yloxycarbonyl)amino-4-phenyl)-butyl]-(3aR,7aS)-thieno[3,2-c]pyridine-(6S)-carboxamide;

N-t-butyl-octahydro-5[2R-hydroxy-3R-N(1',1'-dioxo-2'-methyl-tetrahydrothiophen-3'R-yloxycarbonyl)amino-4-phenylthio)-butyl]-(3aR,7aS)-thieno[3,2-c]pyridine-(6S)-carboxamide;

N-t-butyl-octahydro-5[2R-hydroxy-3R-N(1',1'-dioxo-2'-methyl-tetrahydrothiophen-3'S-yloxycarbonyl)amino-4-phenylthio)-butyl]-(3aR,7aS)-thieno[3,2-c]pyridine-(6S)-carboxamide;

N-t-butyl-octahydro-5[2R-hydroxy-3R-N(1',1'-dioxo-tetrahydrothiophen-2'R-ylmethylcarbonyl)amino-4-phenylthio-butyl]-(3aR,7aS)-thieno[3,2-c]pyridine-(6S)-carboxamide;

N-t-butyl-octahydro-5[2R-hydroxy-3R-N(1',1'-dioxo-tetrahydrothiophen-2'S-ylmethylcarbonyl)amino-4-phenylthio-butyl]-(3aR,7aS)-thieno[3,2-c]pyridine-(6S)-carboxamide;

N-t-butyl-octahydro-5[2R-hydroxy-3R-phenylthiomethyl-4-aza-5-oxo-6S-N(trifluoroacetyl)amino-7-p-fluorophenylsulfonyl-heptyl]-(3aR,7aS)-thieno[3,2-c]pyridine-(6S)-carboxamide.

As noted above, the compounds of the present invention are useful for inhibiting HIV protease, which is an enzyme associated with viral component production and assembly. An embodiment of the present invention is a method of treating or preventing HIV infection comprising administering to a primate in need thereof an effective amount of a compound of formula (I) or a pharmaceutically acceptable salt thereof. Another embodiment of the present invention is a method of treating or preventing AIDS comprising administering to a primate in need thereof an effective amount of a compound of formula (I) or a pharmaceutically acceptable salt thereof. A further embodiment of the present invention is a method of inhibiting HIV replication comprising administering to an HIV infected cell, a cell susceptible to HIV infection or a primate in need thereof, an effective amount of a compound of formula (I) or a pharmaceutically acceptable salt thereof.

The term "effective amount" as used herein, means an amount of a compound of formula (I) which is capable of inhibiting the HIV protease mediated viral component production and assembly. The HIV protease inhibition contemplated by the present method includes either therapeutic or prophylactic treatment, as appropriate. The specific dose of compound administered according to this invention to obtain therapeutic or prophylactic effects will, of course, be determined by the particular circumstances surrounding the case, including, for example, the compound administered, the route of administration, the condition being treated and the individual being treated. A typical daily dose (administered in single or divided doses) will contain a dosage level of from about 0.01 mg/kg to about 50 mg/kg of body weight of an active compound of this invention. Preferred daily doses generally will be from about 0.05 mg/kg to about 20 mg/kg and ideally from about 0.1 mg/kg to about 10 mg/kg.

The compounds can be administered by a variety of routes including oral, rectal, transdermal, subcutaneous, intravenous, intramuscular and intranasal. The compounds of the present invention are preferably formulated prior to administration. Therefore, another embodiment of the present invention is a pharmaceutical formulation comprising an effective amount of a compound of formula (I) or a pharmaceutically acceptable salt thereof and a pharmaceutically acceptable carrier, diluent or excipient therefor.

The active ingredient in such formulations comprises from 0.1% to 99.9% by weight of the formulation. By "pharmaceutically acceptable" it is meant that the carrier, diluent or excipient is compatible with the other ingredients of the formulation and not deleterious to the recipient thereof.

The present pharmaceutical formulations can be prepared by known procedures using known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders and the like.

The following formulation examples are illustrative only and are not intended to limit the scope of the invention in any way. The term "active ingredient" represents a compound of formula (I) or a pharmaceutically acceptable salt thereof.

Formulation 1

Hard gelatin capsules are prepared using the following ingredients:

| | Quantity (mg/capsule) |
|---|---|
| Active ingredient | 250 |
| Starch, dried | 200 |
| Magnesium stearate | 10 |
| Total | 460 mg |

Formulation 2

A tablet is prepared using the ingredients below:

| | Quantity (mg/capsule) |
|---|---|
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

| | Weight |
|---|---|
| Active ingredient | 0.25 |
| Methanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| | Quantity (mg/tablet) |
|---|---|
| Active ingredient | 60 |
| Starch | 45 |
| Microcrystalline cellulose | 35 |
| Polyvinylpyrrolidone (as 10% solution in water) | 4 |
| Sodium carboxymethyl starch | 4.5 |
| Magnesium stearate | 0.5 |
| Talc | 1 |
| Total | 150 |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| | Quantity (mg/capsule) |
|---|---|
| Active ingredient | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 mL dose, are made as follows:

| Active ingredient | 50 mg |
|---|---|
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
|---|---|
| Isotonic saline | 1,000 mL |

The solution of the above ingredients generally is administered intravenously to a subject at a rate of 1 mL per minute.

As noted above, the compounds of formula (I) are useful as HIV protease inhibitors. These compounds may be assayed using two assays: (1) an enzyme inhibition assay, and (2) an antiviral cell culture assay. These assays and the resultant data are provided below.

A Fluorescence HIV-1 Protease Inhibitor Assay was carried out to demonstrate the ability of the compounds of the present invention to inhibit HIV protease. This assay is described in detail in published European Patent Application (EPA) 0 526 009, herein incorporated by reference. Using this assay, a number of the compounds, prepared above, were assayed for HIV protease inhibitory activity.

The concentration of the tested compound that inhibits 50% of the enzyme ($IC_{50}$) is reported below in Table 1. The assay is unable to test compounds at less than a concentration of 0.16 ng/mL. Thus, some values are provided as % inhibition at [the stated] concentration (i.e. $IC_{74}(0.16)$ represents the ability of the compound to inhibit 74% of the enzyme at 0.16 ng/mL).

TABLE 1

Inhibitory Activity of Formula (I) Compounds

| Example No. | Fluorescence Assay $IC_{50}$ in ng/mL |
|---|---|
| 9B-24 mg sample | $IC_{53}$ (0.16) |
| 9B-23 mg sample | 1.6 |
| 10B-52 mg sample | 0.27 |
| 10B-51 mg sample | 0.61 |
| 11C-11 mg sample | 0.91 |
| 11C-6 mg sample | 1.2 |
| 12 | 0.44* (n = 2) |
| 13B-17 mg sample | 1.54 |
| 13B-26 mg sample | $IC_{71}$ (0.16) |
| 14C | 0.15 |
| 15B | 8.7 |
| 17B | $IC_{60}$ (0.16) |
| 17C | $IC_{76}$ (0.16) |
| 19B | 0.16 |
| 19C | $IC_{85}$ (0.16) |
| 21B | 1.3 |
| 22 | 0.89 |
| 23 | 0.85 |
| 24B | 0.09 |
| 25 | 0.17 |
| 26 | 0.29 |
| 27B | |
| 28 | 1.89 |
| 29 | 8.44 |
| 30B | 1.56 |
| 31D-Fraction A | 0.10 |
| 31D-Fraction B | 0.13 |
| 34-Fraction A | 4.47 |
| 34-Fraction B | 16.8 |
| 37C | N.T. |
| 37D | 0.22 |
| 38D | 4.47 |
| 40D | N.T. |

N.T. not tested.
*a calculated average with n number of assays.

In addition, the compounds described in the present application may be tested using an antiviral cell culture assay as described in Weislow, O. S., J. of National Cancer Institute, 81(8), pages 577–586 (Apr. 19, 1989) herein incorporated by reference.

This assay compares the viability of HIV-infected cells in a cell culture medium relative to the viability of such cells in the presence of a test compound. The concentration of test compound necessary to inhibit 90% of the virus is then measured using the viability of the cells as an indicator of viral inhibition. This assay is carried out using cell lines that are sensitive to the lytic effects of HIV infection.

Specifically, this assay utilizes the metabolic reduction of a tetrazolium reagent, 2,3-bis[2-methoxy-4-nitro-5-sulfophenyl]-5-[(phenylamino)carbonyl]-2H-tetrazolium hydroxide (XTT). In the presence of a viable cell, the tetrazolium reagent, XTT, is reduced to provide XTT formazan which may be quantified using colorimetric determination (at 450 nm). The intensity of the chromogenic signal is directly proportional to the concentration of the XTT formazan, thus providing a measure of the quantity of viable cells. The concentration of the tested compound that inhibits 90% of the viral-induced toxicity ($IC_{90}$) is reported below in Table 2.

TABLE 2

Antiviral Activity

| Example No. | IC$_{90}$ in nmol/L |
|---|---|
| 9B-24 mg sample | 78 |
| 9B-23 mg sample | 604 |
| 10B-52 mg sample | 9 |
| 10B-51 mg sample | 77 |
| 11C-11 mg sample | 26 |
| 11C-6 mg sample | 29 |
| 12 | 96 |
| 13B-17 mg sample | 880 |
| 13B-26 mg sample | 90 |
| 14C | 28 |
| 15B | 7630 |
| 17B | 78* (n = 2) |
| 17C | 31* (n = 3) |
| 19B | 233 |
| 19C | 52* (n = 4) |
| 21B | 78 |
| 22 | 296 |
| 23 | |
| 24B | 81.8 |
| 25 | 279 |
| 26 | 225 |
| 27B | |
| 28 | 21.8 |
| 29 | 754 |
| 30B | 203 |
| 31D-Fraction A | 30.3 |
| 31D-Fraction B | 31.4 |
| 34-Fraction A | 45.2 |
| 34-Fraction B | 32.1 |
| 37C | N.T. |
| 37D | 1.8 |
| 38D | 7.1 |
| 40D | 7.1 |

We claim:

1. A compound of formula (I)

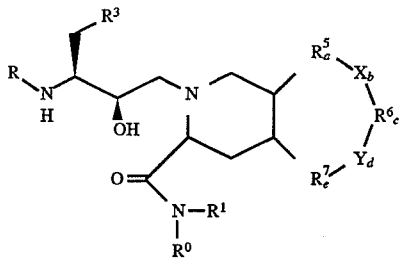

wherein:

R is a group having the formula:

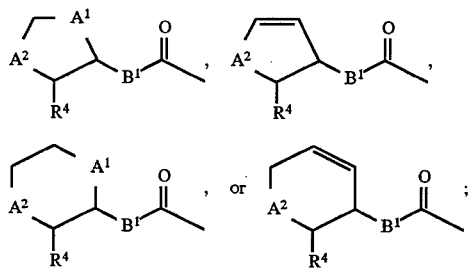

$A^1$ and $A^2$ are independently —C—, —O—, —S—, —S(O)—, —S(O)$_2$—, —NH— or —N(CH$_3$)—;

$B^1$ is —O—, —S—, —CH$_2$—, —CH$_2$—CH$_2$—, —NH—, or —N(CH$_3$)—;

$R^4$ is $C_1$–$C_6$ alkyl;

$R^3$ is —(CH$_2$)$_i$—R$^{3a}$;

i is 0, 1, 2, 3, or 4;

$R^{3a}$ is aryl, —O-aryl, or —S-aryl;

$R^0$ and $R^1$ are independently hydrogen, $C_1$–$C_6$ alkyl, or hydroxy($C_1$–$C_6$)alkyl;

a, c and e are each independently 0, 1 or 2;

b and d are each independently 0 or 1;

each $R^5$ is independently —CH$_2$—, —CHR$^{5x}$—, or —CR$^{5x}$R$^{5x}$—;

each $R^6$ is independently —CH$_2$—, —CHR$^{6x}$—, or —CR$^{6x}$R$^{6x}$—;

each $R^7$ is independently —CH$_2$—, —CHR$^{7x}$—, or —CR$^{7x}$R$^{7x}$—;

each of $R^{5x}$, $R^{6x}$, and $R^{7x}$ is independently selected from the group consisting of halo, hydroxy, $C_1$–$C_6$ alkyl, halo($C_1$–$C_6$)alkyl, hydroxy($C_1$–$C_6$)alkyl, $C_1$–$C_6$ alkoxy, $C_1$–$C_6$ alkylthio, $C_1$–$C_6$ alkylthio ($C_1$–$C_6$)alkyl, amino, or cyano;

X and Y are independently —S—, —S(O)—, —S(O)$_2$—, —O—, —NH—, or —N(R$^9$)—; and $R^9$ is $C_1$–$C_6$ alkyl, aryl($C_1$–$C_6$)alkyl, aryl, arylcarbonyl, formyl, or $C_2$–$C_6$ alkanoyl;

with the provisos that:

b and d cannot both be 0;

the sum of a, b, c, d and e must be 2, 3, 4 or 5;

if $R^5$ is —CR$^{5x}$R$^{5x}$—, then $R^6$ must be —CH$_2$— or —CHR$^{6x}$—; and $R^7$ must be —CH$_2$— or —CHR$^{7x}$—;

if $R^6$ is —CR$^{6x}$R$^{6x}$—, then $R^5$ must be —CH$_2$— or —CHR$^{5x}$—; and $R^7$ must be —CH$_2$— or —CHR$^{7x}$—;

if $R^7$ is —CR$^{7x}$R$^{7x}$—, then $R^5$ must be —CH$_2$— or —CHR$^{5x}$—; and $R^6$ must be —CH$_2$— or —CHR$^{6x}$—;

or a pharmaceutically acceptable salt thereof.

2. A compound according to claim 1 wherein the compound is of the formula:

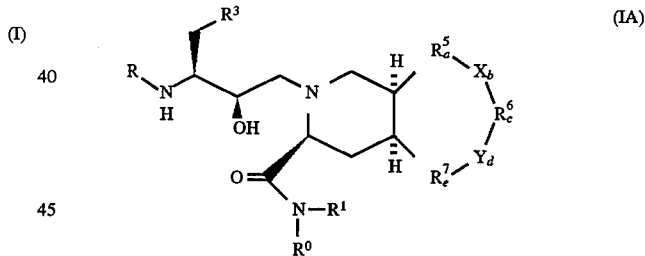

or a pharmaceutically acceptable salt thereof.

3. A compound according to claim 2 where:

the sum of a, b, c, d, and e is 3 or 4;

R is a group of the formula:

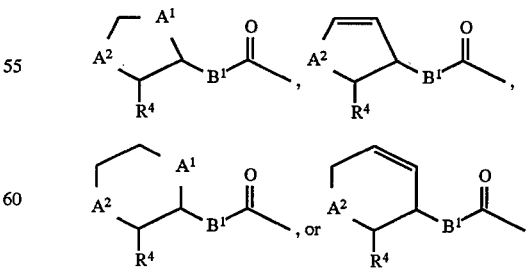

$A^1$ is —C—, —O—, —S—, —S(O)$_2$—;

$A^2$ is —C—, —O—, —S—, or —S(O)$_2$—;

$B^1$ is —O—, —CH$_2$—, or —NH—;

$R^3$ is —$(CH_2)$—$R^{3a}$;

$R^{3a}$ is aryl, or —S-aryl;

$R^0$ and $R^1$ are independently hydrogen, or $C_1$–$C_6$ alkyl;

each of $R^{5x}$, $R^{6x}$, and $R^{7x}$ is independently selected from the group consisting of halo, $C_1$–$C_6$ alkyl, hydroxy($C_1$–$C_4$)alkyl or $C_1$–$C_4$ alkylthio; and X and Y are independently —S—, —O—, or —NH—;

or a pharmaceutically acceptable salt thereof.

4. A compound according to claim 3 where:

one of b and d is 0;

$A^1$ is —C—, —$S(O)_2$—;

$A^2$ is —C—, —O—, —S—, or —$S(O)_2$—; and $B^1$ is —O—, or —$CH_2$—;

or a pharmaceutically acceptable salt thereof.

5. A compound according to claim 4 which is N-t-butyl-octahydro-5[2R-hydroxy-3R-N(1',1'-dioxo-2'R-isopropyl-tetrahydrothiophen-3'R-yloxycarbonyl)amino-4-phenylthio-)-butyl]-(3aR,7aS)-thieno[3,2-c]pyridine-(6S)-carboxamide; or a pharmaceutically acceptable salt.

6. A compound according to claim 4 which is N-t-butyl-octahydro-5[2R-hydroxy-3R-N(2'R-isopropyl-tetrahydrothiophen-3'R-yloxycarbonyl)amino-4-phenylthio-)-butyl]-(3aR,7aS)-thieno[3,2-c]pyridine-(6S)-carboxamide; or a pharmaceutically acceptable salt.

7. A compound according to claim 4 which is N-t-butyl-octahydro-5[2R-hydroxy-3R-N(1',1'-dioxo-tetrahydrothiophen-3'R-yloxycarbonyl)amino-4-phenylthio)butyl]-(3aR,7aS)-thieno[3,2-c]pyridine-(6S)-carboxamide; or a pharmaceutically acceptable salt.

8. A compound according to claim 4 which is N-t-butyl-octahydro-5[2R-hydroxy-3R-N(1',1'-dioxo-tetrahydrothiophen-3'R-ylmethylcarbonyl)amino-4-phenylthio-butyl]-(3aR,7aS)-thieno[3,2-c]pyridine-(6S)-carboxamide; or a pharmaceutically acceptable salt.

9. A compound according to claim 4 which is N-t-butyl-octahydro-5[2R-hydroxy-3R-N(2'S-methyl-tetrahydrofuran-3'S-yloxycarbonyl)amino-4-phenylthio-)butyl]-(3aR,7aS)-thieno[3,2-c]pyridine-(6S)-carboxamide; or a pharmaceutically acceptable salt.

10. A pharmaceutical formulation comprising one or more pharmaceutically acceptable carriers, diluents or excipients and a compound of claim 1.

11. A pharmaceutical formulation according to claim 10 where the compound is of the formula:

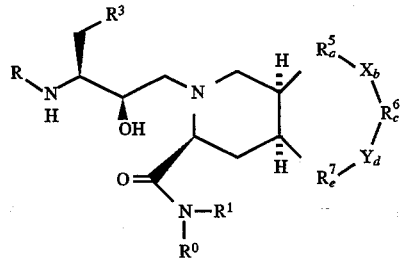

or a pharmaceutically acceptable salt thereof.

12. A pharmaceutical formulation according to claim 11 where the compound is one wherein:

the sum of a, b, c, d, and e is 3 or 4;

R is a group of the formula:

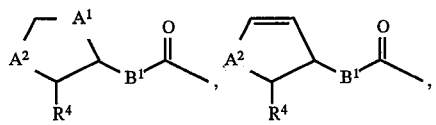

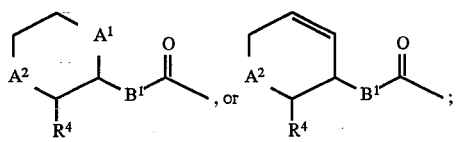

$A^1$ is —C—, —O—, —S—, —$S(O)_2$—;

$A^2$ is —C—, —O—, —S—, or —$S(O)_2$—;

$B^1$ is —O—, —$CH_2$—, or —NH—;

$R^3$ is —$(CH_2)$—$R^{3a}$;

$R^{3a}$ is aryl, or —S-aryl;

$R^0$ and $R^1$ are independently hydrogen, or $C_1$–$C_6$ alkyl;

each of $R^{5x}$, $R^{6x}$, and $R^{7x}$ is independently selected from the group consisting of halo, $C_1$–$C_6$ alkyl, hydroxy($C_1$–$C_4$)alkyl or $C_1$–$C_4$ alkylthio; and X and Y are independently —S—, —O—, or —NH—;

or a pharmaceutically acceptable salt thereof.

13. A pharmaceutical formulation according to claim 12 where the compound is one wherein:

one of b and d is 0;

$A^1$ is —C—, —$S(O)_2$—;

$A^2$ is —C—, —O—, —S—, or —$S(O)_2$—; and $B^1$ is —O—, or —$CH_2$—;

or a pharmaceutically acceptable salt thereof.

14. A pharmaceutical formulation according to claim 13 wherein the compound is N-t-butyl-octahydro-5[2R-hydroxy-3R-N(1',1'-dioxo-2'R-isopropyl-tetrahydrothiophen-3'R-yloxycarbonyl)amino-4-phenylthio-)-butyl]-(3aR,7aS)-thieno[3,2-c]pyridine-(6S)-carboxamide; or a pharmaceutically acceptable salt.

15. A pharmaceutical formulation according to claim 13 wherein the compound is N-t-butyl-octahydro-5[2R-hydroxy-3R-N(2'R-isopropyl-tetrahydrothiophen-3'R-yloxycarbonyl)amino-4-phenylthio-)-butyl]-(3aR,7aS)-thieno[3,2-c]pyridine-(6S)-carboxamide; or a pharmaceutically acceptable salt.

16. A pharmaceutical formulation according to claim 13 wherein the compound is N-t-butyl-octahydro-5[2R-hydroxy-3R-N(1',1'-dioxo-tetrahydrothiophen-3'R-yloxycarbonyl)amino-4-phenylthio)-butyl]-(3aR,7aS)-thieno[3,2-c]pyridine-(6S)-carboxamide; or a pharmaceutically acceptable salt.

17. A pharmaceutical formulation according to claim 13 wherein the compound is N-t-butyl-octahydro-5[2R-hydroxy-3R-N(1',1'-dioxo-tetrahydrothiophen-3'R-ylmethylcarbonyl)amino-4-phenylthio-butyl]-(3aR,7aS)-thieno[3,2-c]pyridine-(6S)-carboxamide; or a pharmaceutically acceptable salt.

18. A pharmaceutical formulation according to claim 13 wherein the compound is N-t-butyl-octahydro-5[2R-hydroxy-3R-N(2'S-methyl-tetrahydrothiofuran-3'S-yloxycarbonyl)amino-4-phenylthio-)-butyl]-(3aR,7aS)-thieno[3,2-c]pyridine-(6S)-carboxamide; or a pharmaceutically acceptable salt.

19. A method of treating HIV infection comprising administering to a primate in need thereof an effective amount of a compound of claim 1.

20. A method according to claim 19 where the compound is of the formula:

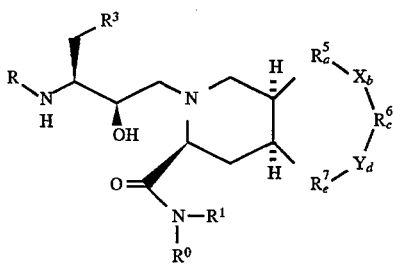

(IA)

or a pharmaceutically acceptable salt thereof.

21. A method according to claim 20 where the compound is one wherein:
the sum of a, b, c, d, and e is 3 or 4;
R is a group of the formula:

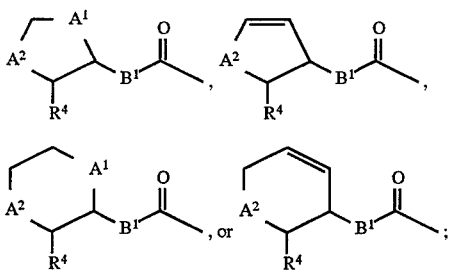

$A^1$ is —C—, —O—, —S—, —S(O)$_2$—;
$A^2$ is —C—, —O—, —S—, or —S(O)$_2$—;
$B^1$ is —O—, —CH$_2$—, or —NH—;
$R^3$ is —(CH$_2$)—$R^{3a}$;
$R^{3a}$ is aryl, or —S-aryl;
$R^0$ and $R^1$ are independently hydrogen, or C$_1$-C$_6$ alkyl; each of $R^{5x}$, $R^{6x}$, and $R^{7x}$ is independently selected from the group consisting of halo, C$_1$-C$_6$ alkyl, hydroxy(C$_1$-C$_4$)alkyl or C$_1$-C$_4$ alkylthio; and
X and Y are independently —S—, —O—, or —NH—;
or a pharmaceutically acceptable salt thereof.

22. A method according to claim 21 where the compound is one wherein:
one of b and d is 0;
$A^1$ is —C—, —S(O)$_2$—;
$A^2$ is —C—, —O—, —S—, or —S(O)$_2$—; and
$B^1$ is —O—, or —CH$_2$—;
or a pharmaceutically acceptable salt thereof.

23. A method according to claim 22 wherein the compound is N-t-butyl-octahydro-5[2R-hydroxy-3R-N(1',1'-dioxo-2'R-isopropyl-tetrahydrothiophen-3'R-yloxycarbonyl)amino-4-phenylthio-)-butyl]-(3aR,7aS)-thieno[3,2-c]pyridine-(6S)-carboxamide; or a pharmaceutically acceptable salt.

24. A method according to claim 22 wherein the compound is N-t-butyl-octahydro-5[2R-hydroxy-3R-N(2'R-isopropyl-tetrahydrothiophen-3'R-yloxycarbonyl)amino-4-phenylthio-)-butyl]-(3aR,7aS)-thieno[3,2-c]pyridine-(6S)-carboxamide; or a pharmaceutically acceptable salt.

25. A method according to claim 22 wherein the compound is N-t-butyl-octahydro-5[2R-hydroxy-3R-N(1',1'-dioxo-tetrahydrothiophen-3'R-yloxycarbonyl)amino-4-phenylthio)-butyl]-(3aR,7aS)-thieno[3,2-c]pyridine-(6S)-carboxamide; or a pharmaceutically acceptable salt.

26. A method according to claim 22 wherein the compound is N-t-butyl-octahydro-5[2R-hydroxy-3R-N(1',1'-dioxo-tetrahydrothiophen-3'R-ylmethylcarbonyl)amino-4-phenylthio-butyl]-(3aR,7aS)-thieno[3,2-c]pyridine-(6S)-carboxamide; or a pharmaceutically acceptable salt.

27. A method according to claim 22 wherein the compound is N-t-butyl-octahydro-5[2R-hydroxy-3R-N(2'S-methyl-tetrahydrofuran-3'S-yloxycarbonyl)amino-4-phenylthio-)-butyl]-(3aR,7aS)-thieno[3,2-c]pyridine-(6S)-carboxamide; or a pharmaceutically acceptable salt.

28. A method of inhibiting HIV replication comprising administering to an HIV infected cell, a cell susceptible to HIV infection or a primate in need thereof, an effective amount of a compound of claim 1.

29. A method according to claim 28 where the compound is of the formula:

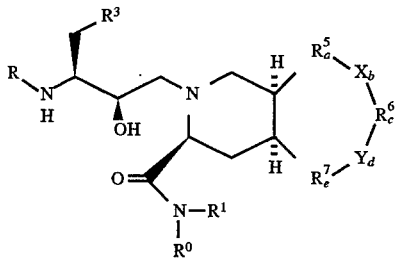

(IA)

or a pharmaceutically acceptable salt thereof.

30. A method according to claim 29 where the compound is one wherein:
the sum of a, b, c, d, and e is 3 or 4;
R is a group of the formula:

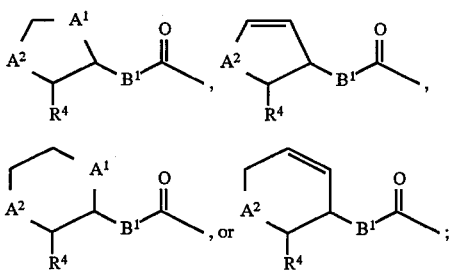

$A^1$ is —C—, —O—, —S—, —S(O)$_2$—;
$A^2$ is —O—, —S—, or —S(O)$_2$—;
$B^1$ is —O—, —CH$_2$—, or —NH—;
$R^3$ is —(CH$_2$)—$R^{3a}$;
$R^{3a}$ is aryl, or —S-aryl;
$R^0$ and $R^1$ are independently hydrogen, or C$_1$-C$_6$ alkyl; each of $R^{5x}$, $R^{6x}$, and $R^{7x}$ is independently selected from the group consisting of halo, C$_1$-C$_6$ alkyl, hydroxy(C$_1$-C$_4$)alkyl or C$_1$-C$_4$ alkylthio; and
X and Y are independently —S—, —O—, or —NH—;
or a pharmaceutically acceptable salt thereof.

31. A method according to claim 30 where the compound is one wherein:
one of b and d is 0;
$A^1$ is —C—, —S(O)$_2$—;
$A^2$ is —C—, —O—, —S—, or —S(O)$_2$—; and
$B^1$ is —O—, or —CH$_2$—;
or a pharmaceutically acceptable salt thereof.

32. A method according to claim 31 wherein the compound is N-t-butyl-octahydro-5[2R-hydroxy-3R-N(1',1'-dioxo-2'R-isopropyl-tetrahydrothiophen-3'R-yloxycarbonyl)amino-4-phenylthio-)-butyl]-(3aR,7aS)-thieno[3,2-c]pyridine-(6S)-carboxamide; or a pharmaceutically acceptable salt.

33. A method according to claim 31 wherein the compound is N-t-butyl-octahydro-5[2R-hydroxy-3R-N(2'R-isopropyl-tetrahydrothiophen-3'R-yloxycarbonyl)amino-4-phenylthio-)-butyl]-(3aR,7aS)-thieno[3,2-c]pyridine-(6S)-carboxamide; or a pharmaceutically acceptable salt.

34. A method according to claim 31 wherein the compound is N-t-butyl-octahydro-5[2R-hydroxy-3R-N(1',1'-dioxo-tetrahydrothiophen-3'R-yloxycarbonyl)amino-4-phenylthio)-butyl]-(3aR,7aS)-thieno[3,2-c]pyridine-(6S)-carboxamide; or a pharmaceutically acceptable salt.

35. A method according to claim 31 wherein the compound is N-t-butyl-octahydro-5[2R-hydroxy-3R-N(1',1'-dioxo-tetrahydrothiophen-3'R-ylmethylcarbonyl)amino-4-phenylthio-butyl]-(3aR,7aS)-thieno[3,2-c]pyridine-(6S)-carboxamide; or a pharmaceutically acceptable salt.

36. A method according to claim 31 wherein the compound is N-t-butyl-octahydro-5[2R-hydroxy-3R-N(2'S-methyl-tetrahydrofuran-3'S-yloxycarbonyl)amino-4-phenylthio-)-butyl]-(3aR,7aS)-thieno[3,2-c]pyridine-(6S)-carboxamide; or a pharmaceutically acceptable salt.

* * * * *